(12) United States Patent
Yan et al.

(10) Patent No.: US 12,145,917 B2
(45) Date of Patent: Nov. 19, 2024

(54) CRYSTALLINE FORMS OF A COMPOUND FOR TREATING OR PREVENTING GOUT OR HYPERURICEMIA

(71) Applicant: Arthrosi Therapeutics, Inc., Laguna Hills, CA (US)

(72) Inventors: Shunqi Yan, Laguna Hills, CA (US); Litain Yeh, Laguna Hills, CA (US); Zheng Jane Li, Beijing (CN); Ruiping Wang, Beijing (CN)

(73) Assignee: ARTHROSI THERAPEUTICS, INC., San Diego, CA (US)

( * ) Notice: Subject to any disclaimer, the term of this patent is extended or adjusted under 35 U.S.C. 154(b) by 653 days.

(21) Appl. No.: 17/311,249

(22) PCT Filed: Dec. 5, 2019

(86) PCT No.: PCT/US2019/064784
§ 371 (c)(1),
(2) Date: Jun. 4, 2021

(87) PCT Pub. No.: WO2020/118113
PCT Pub. Date: Jun. 11, 2020

(65) Prior Publication Data
US 2022/0024889 A1    Jan. 27, 2022

(51) Int. Cl.
*C07D 307/80* (2006.01)
*A61K 45/06* (2006.01)

(52) U.S. Cl.
CPC ............ *C07D 307/80* (2013.01); *A61K 45/06* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 4,327,725 A | 5/1982 | Cortese et al. | |
| 4,624,848 A | 11/1986 | Lee | |
| 4,968,509 A | 11/1990 | Radebaugh et al. | |
| 5,323,907 A | 6/1994 | Kalvelage | |
| 5,456,923 A | 10/1995 | Nakamichi et al. | |
| 5,461,140 A | 10/1995 | Heller et al. | |
| 5,516,527 A | 5/1996 | Curatolo | |
| 5,622,721 A | 4/1997 | Dansereau et al. | |
| 5,686,105 A | 11/1997 | Kelm et al. | |
| 5,700,410 A | 12/1997 | Nakamichi et al. | |
| 5,977,175 A | 11/1999 | Lin | |

(Continued)

FOREIGN PATENT DOCUMENTS

| CN | 104262305 A | 1/2015 |
|---|---|---|
| CN | 104311516 A | 1/2015 |

(Continued)

OTHER PUBLICATIONS

Braga et al., Chem. Commun., 2005, 3635-3645 (Year: 2005).*

(Continued)

*Primary Examiner* — Jeffrey S Lundgren
*Assistant Examiner* — Anthony Joseph Seitz
(74) *Attorney, Agent, or Firm* — WILSON SONSINI GOODRICH & ROSATI

(57) ABSTRACT

Described herein are crystalline forms of (3,5-dibromo-4-hydroxyphenyl)(2-(1-hydroxyethyl)benzofuran-3-yl-4,5,6,7-$d_4$)methanone, and solvates thereof.

18 Claims, 6 Drawing Sheets

(56) References Cited

U.S. PATENT DOCUMENTS

| | | | |
|---|---|---|---|
| 6,465,014 | B1 | 10/2002 | Moroni et al. |
| 6,932,983 | B1 | 8/2005 | Straub et al. |
| 10,005,750 | B2 | 6/2018 | Wempe et al. |
| 10,239,854 | B2 | 3/2019 | Yan et al. |
| 10,508,093 | B2 | 12/2019 | Yan et al. |
| 2007/0185195 | A1 | 8/2007 | Endou et al. |
| 2008/0305169 | A1 | 12/2008 | Miki et al. |
| 2012/0184587 | A1 | 7/2012 | Kobashi et al. |
| 2013/0225673 | A1 | 8/2013 | Wempe et al. |
| 2014/0128438 | A1 | 5/2014 | Lavan et al. |
| 2014/0128460 | A1 | 5/2014 | Hegde |
| 2014/0357683 | A1 | 12/2014 | Gunawardhana et al. |
| 2015/0031768 | A1 | 1/2015 | Groves et al. |
| 2016/0031879 | A1 | 2/2016 | Karra et al. |
| 2017/0349562 | A1 | 12/2017 | Hegde |
| 2019/0040030 | A1 | 2/2019 | Yan et al. |
| 2020/0148659 | A1 | 5/2020 | Yan et al. |
| 2022/0023251 | A1 | 1/2022 | Yan et al. |
| 2022/0112171 | A1 | 4/2022 | Yan et al. |
| 2022/0242841 | A1 | 8/2022 | Yan et al. |
| 2023/0218563 | A1 | 7/2023 | Yeh et al. |
| 2024/0116888 | A1 | 4/2024 | Yan et al. |

FOREIGN PATENT DOCUMENTS

| | | | | |
|---|---|---|---|---|
| CN | 104736178 | A | 6/2015 | |
| CN | 111763215 | A | 10/2020 | |
| CN | 112079830 | A | 12/2020 | |
| DE | 19624292 | A1 | 1/1998 | |
| JP | 2010525081 | A | 7/2010 | |
| JP | 2013539757 | A | 10/2013 | |
| WO | WO-2008150118 | A2 | 12/2008 | |
| WO | WO-2009143020 | A1 | 11/2009 | |
| WO | WO-2011141419 | A1 | 11/2011 | |
| WO | WO-2012048058 | A2 | 4/2012 | |
| WO | WO-2014149789 | A1 | 9/2014 | |
| WO | WO-2015134467 | A1 | 9/2015 | |
| WO | WO-2018017368 | A1 * | 1/2018 | A61K 31/343 |
| WO | WO-2018090921 | A1 | 5/2018 | |
| WO | WO-2018110887 | A1 | 6/2018 | |
| WO | WO-2019195118 | A1 | 10/2019 | |
| WO | WO-2019233459 | A1 | 12/2019 | |
| WO | WO-2020070539 | A1 | 4/2020 | |
| WO | WO-2020118113 | A1 | 6/2020 | |
| WO | WO-2020118114 | A1 | 6/2020 | |
| WO | WO-2020219904 | A1 | 10/2020 | |
| WO | WO-2020232156 | A1 | 11/2020 | |
| WO | WO-2021252630 | A1 | 12/2021 | |
| WO | WO-2022134939 | A1 | 6/2022 | |
| WO | WO-2022143104 | A1 | 7/2022 | |
| WO | WO-2023028054 | A1 | 3/2023 | |
| WO | WO-2023098872 | A1 * | 6/2023 | |
| WO | WO-2023125667 | A1 | 7/2023 | |

OTHER PUBLICATIONS

Blake et al., Studies with Deuterated Drugs. J. Pharm. Sci. 64(3):367-391 (1975).

Buteau. Deuterated drugs: unexpectedly nonobvious. J High Tech L 10:22 (2009).

CAS Registry 7342-11-2; 1068709-24-9; 121887-11-4; 1134336-43-8 (Apr. 14, 2009).

Chen et al. A cell line stably expressing lentivirus-mediated hURAT1 as an in vitro model of screening uricosuric agents. Life Sciences 20(3):248-254 (2016) (English Abstract).

Hirayama Yoshinaki. Organic Compound Crystal Production Handbook. pp. 1-17, 37, 40, 45, 51,57 & 65 (2008).

Kawaguchi et al., Drug and crystal polymorphism. Journal Human environment engineering. 4(2):310-17 (2002).

Liang et al. Tuning the stability of alkoxyisopropyl protection groups. Beilstein J Org Chem 15:746-751 (2019).

O'Brien et al. Chapter 30: In Vitro Cytotoxicity Assessment. High Content Screening: A Powerful Approach to Systems Cell Biology and Drug Discovery Ed. Taylor et al. (pp. 415-425) (2007).

PCT/CN2022/136194 International Search Report and Written Opinion dated Mar. 1, 2023.

PCT/CN2022/142846 International Search Report and Written Opinion dated Mar. 22, 2022.

Shin et al. Interactions of urate transporter URAT1 in human kidney with uricosuric drugs. Nephrology 16(2):156-162 (2011).

Wako Organic Square No. 33:2-20. Available at https://labchem-wako.fujifilm.com/jp/journal/docs/org33.pdf (Sep. 2010).

Zhou et al. A study comparing the safety and efficacy of febuxostat, allopurinol, and benzbromarone in Chinese gout patients: a retrospective cohort study. Int J Clin Pharmacol 55(2):163-168 (2017).

Arnold et al. Liquid chromatography-mass spectrometry in metabolic research. I. Metabolites of benzbromarone in human plasma and urine. Journal of Chromatography 554(1-2):267-80 (1991).

Bernstein. Crystal Structure Prediction and Polymorphism. ACA Transactions 39:14-23 (2004).

Braga et al. Making crystals from crystals: a green route to crystal engineering and polymorphism. J. Royal Soc. Chem. Commun 29:3635-3645 (2005).

Bush et al. Substrate probes for the mechanism of aromatic hydroxylation catalyzed by cytochrome P-450: selectively deuterated analogs of warfarin. Journal of medicinal chemistry 28.8:992-996 (1985).

Cho et al. Identification of novel glutathione adducts of benzbromarone in human liver microsomes. Drug Metabolism and Pharmacokinetics 32(1):46-52 (2017).

Darbyshire et al. Substrate probe for the mechanism of aromatic hydroxylation catalyzed by cytochrome P450. Drug metabolism and disposition 24(9):1038-1045 (1996).

De Vries et al. Benzbromarone hydroxylation in man: defective formation of the 6-hydroxybenzbromarone metabolite. The Clinical investigator 71(11):947-52 (1993).

De Vries et al. Metabolism of benzbromarone in man: structures of new oxidative metabolites, 6-hydroxy- and 1'-oxo-benzbromarone, and the enantioselective formation and elimination of 1'-hydroxybenzbromarone. Xenobiotica 23(12):1435-50 (1993).

De Vries et al. The isolation, identification and structure of a new hydroxylated metabolite of benzbromarone in man. Xenobiotica 19(12):1461-70 (1989).

Gannett et al. Synthesis of deuterated naproxens. Journal of Labelled Compounds and Radiopharmaceuticals: The Official Journal of the International Isotope Society 50(14):1272-1275 (2007).

Heimark et al. The synthesis of deuterium labelled metabolites of warfarin and phenprocoumon. Journal of Labelled Compounds and Radiopharmaceuticals 23(2):137-148 (1986).

International Conference on Harmonization of Technical Requirements for Registration of Pharmaceuticals for Human Use (ICH), "Impurities: Guidelines for Residual Solvents Q3C(R6)." (Oct. 2016).

Iwamura et al. CYP2C9-mediated metabolic activation of losartan detected by a highly sensitive cell-based screening assay. Drug Metab Dispos 39(5):838-846 (2011).

Jones et al. Pharmaceutical Cocrystals: An Emerging Approach to Physical Property Enhancement. MRS Bulletin 31:875-879 (2006).

Kitagawara et al. Novel Bioactivation Pathway of Benzbromarone Mediated by Cytochrome P450. Drug Metab Dispos 43:1303-1306 (2015).

Kobayashi et al. Cytotoxic effects of benzbromarone and its 1'-hydroxy metabolite in human hepatocarcinoma FLC4 cells cultured on micro-space cell culture plates. Drug metabolism and pharmacokinetics 28(3):265-8 (2013).

Kobayashi et al. Identification of CYP isozymes involved in benzbromarone metabolism in human liver microsomes. From Biopharmaceutics & Drug Disposition 33(8):466-473 (2012).

Lee et al. A benefit-risk assessment of benzbromarone in the treatment of gout. Was its withdrawal from the market in the best interest of patients? Drug Safety 31(8):643-665 (2008).

Leroy et al. Synthesis of deuterium-labelled diclofenac sodium. Journal of Labelled Compounds and Radiopharmaceuticals 33(11):1019-1027 (1993).

Liberman et al. Pharmaceutical Dosage Forms. 2nd Ed. 1:209-214 (1990).

(56) References Cited

OTHER PUBLICATIONS

Locuson et al. Charge and Substituent Effects on Affinity and Metabolism of Benzbromarone-Based CYP2C19 Inhibitors. J Med Chem 47(27):6768-6776 (2004).

Maurer et al. Urinary metabolites of benzbromarone in man. Arzneimittel-Forschung 40(4):460-2 (1990).

McDonald et al. Sequential Metabolism and Bioactivation of the Hepatotoxin Benzbromarone: Formation of Glutathione Adducts From a Catechol Intermediate. Chem Res. Toxicol 20:1833-1842 (2007).

PCT/US2017/041763 International Search Report and Written Opinion dated Oct. 20, 2017.

PCT/US2019/064784 International Search Report and Written Opinion dated Feb. 25, 2020.

PCT/US2019/064785 International Search Report and Written Opinion dated Feb. 25, 2020.

Price. The computational prediction of pharmaceutical crystal structures and polymorphism. Advanced Drug Delivery Reviews 56:301-319 (2004).

SciFinder Search 2018 (358 pages).

Singh et al. Encyclopedia of Pharmaceutical Technology 2nd Ed. pp. 751-753 (2002).

Uchida et al. Benzbromarone Pharmacokinetics and Pharmacodynamics in Different Cytochrome P450 2C9 Genotypes. Drug Metab Pharmacokinet 25(6):605-610 (2010).

U.S. Appl. No. 16/268,367 Office Action dated May 9, 2019.

U.S. Appl. No. 16/684,046 Office Action dated Jun. 16, 2021.

Walter-Sack et al. Biliary excretion of benzbromarone and its hydroxylated main metabolites in humans. European Journal of Medical Research 3(1/2):45-49 (1998).

Walter-Sack et al. Rapid and slow benzbromarone elimination phenotypes in man: benzbromarone and metabolite profiles. European Journal of Clinical Pharmacology 39(6):577-81 (1990).

Waterhouse. Synthesis of deuterium labelled 4'-hydroxydiclofenac. Journal of Labelled Compounds and Radiopharmaceuticals: The Official Journal of the International Isotope Society 42(11):1075-1083 (1999).

Wu et al. Metabolism studies of benzbromarone in rats by high performance liquid chromatography-quadrupole time of flight mass spectrometry. Journal of Chromatography B: Analytical Technologies in the Biomedical and Life Sciences 911:122-132 (2012).

Wu et al. Synthesis of deuterium labelled 4'-hydroxy diclofenac with improved isotopic enrichment. Journal of labelled compounds and radiopharmaceuticals. 52(13):535-537 (2009).

Berge et al. Pharmaceutical Salts. Journal of Pharmaceutical Sciences 66(1):1-19 (Jan. 1977).

PCT/US2020/032725 International Invitation to Pay Additional Fees dated Jul. 27, 2020.

PCT/US2020/032725 International Search Report and Written Opinion dated Sep. 28, 2020.

PCT/US2021/036620 International Search Report and Written Opinion dated Sep. 15, 2021.

PUBCHEM compound ID 131667680 [https://pubchem.ncbi.nlm.nih.gov/compound/131667680] (2017).

PCT/US2022/041218 International Search Report and Written Opinion dated Oct. 7, 2022.

Takata. API form Screening and selection in the stage of drug development. Pharm Stage 6(10):20-25 (2007).

U.S. Appl. No. 17/311,245 Office Action dated Jul. 1, 2024.

Walter-Sack, I. et al. Benzbromarone Disposition and Uricosuric Action; Evidence for Hydroxilation Instead of Debromination to Benzarone. Klin Wochenschr 66(4):160-166 (1988).

Hosoya, Tatsuo et al. Dotinurad versus benzbromarone in Japanese hyperuricemic patient with or without gout: a randomized, double-blind, parallel-group, phase 3 study. Clinical and experimental nephrology 24(Suppl 1):S62-S70 (2020).

Yu, Kuang-Hui et al. Management of gout and hyperuricemia: Multidisciplinary consensus in Taiwan. International journal of rheumatic diseases 21(4):772-787 (2018).

\* cited by examiner

CRYSTALLINE FORMS OF A COMPOUND FOR TREATING OR PREVENTING GOUT OR HYPERURICEMIA

CROSS-REFERENCE

This application claims benefit of PCT/CN2018/119567, filed on Dec. 6, 2018, which is herein incorporated by reference in its entirety.

BACKGROUND

Hyperuricemia is caused by the overproduction or under-excretion of uric acid, and is considered to be a causative factor of several diseases that significantly impair the quality of life. For example, hyperuricemia is considered the causative factor of gout—the most prevalent form of inflammatory arthritis, characterized by severe pain and tenderness in joints caused by urate crystal accumulation. The identification of a gout/hyperuricemia drug effective in lowering serum uric acid (sUA) with reduced toxicity represents an unmet medical need that would have beneficial impact on patients.

SUMMARY OF THE INVENTION

In one aspect, described herein is a crystalline form of (3,5-dibromo-4-hydroxyphenyl)(2-(1-hydroxyethyl)benzofuran-3-yl-4,5,6,7-$d_4$)methanone, or solvate thereof.

In one embodiment, is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form of (3,5-dibromo-4-hydroxyphenyl)(2-(1-hydroxyethyl)benzofuran-3-yl-4,5,6,7-$d_4$)methanone is Form 3 having at least one of the following properties:
  (a) an X-ray powder diffraction (XRPD) pattern substantially the same as shown in FIG. 1;
  (b) an X-ray powder diffraction (XRPD) pattern with characteristic peaks at 6.8° 2-Theta, 13.6° 2-Theta, 14.6° 2-Theta, 21.2° 2-Theta, 24.2° 2-Theta, 24.7° 2-Theta, 26.7° 2-Theta, and 27.5° 2-Theta;
  (c) a thermo-gravimetric analysis (TGA) substantially similar to the one set forth in FIG. 2;
  (d) a DSC thermogram substantially similar to the one set forth in FIG. 3;
  (e) a DSC thermogram with an endotherm having an onset at about 147° C.;
  (f) non-hygroscopicity; or
  (g) combinations thereof.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form has an X-ray powder diffraction (XRPD) pattern substantially the same as shown in FIG. 1.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form has an X-ray powder diffraction (XRPD) pattern with characteristic peaks at 6.8° 2-Theta, 13.6° 2-Theta, 14.6° 2-Theta, 21.2° 2-Theta, 24.2° 2-Theta, 24.7° 2-Theta, 26.7° 2-Theta, and 27.5° 2-Theta.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form has a thermogravimetric analysis (TGA) substantially similar to the one set forth in FIG. 2.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form has a DSC thermogram substantially similar to the one set forth in FIG. 3.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form has a DSC thermogram with an endotherm having an onset at about 147° C.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form is non-hygroscopic.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form is characterized as having properties: (a) an X-ray powder diffraction (XRPD) pattern substantially the same as shown in FIG. 1; (b) an X-ray powder diffraction (XRPD) pattern with characteristic peaks at 6.8° 2-Theta, 13.6° 2-Theta, 14.6° 2-Theta, 21.2° 2-Theta, 24.2° 2-Theta, 24.7° 2-Theta, 26.7° 2-Theta, and 27.5° 2-Theta; (c) a thermogravimetric analysis (TGA) substantially similar to the one set forth in FIG. 2; (d) a DSC thermogram substantially similar to the one set forth in FIG. 3; (e) a DSC thermogram with an endotherm having an onset at about 147° C.; and (f) non-hygroscopicity.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form is obtained from toluene, toluene/heptane, or ethyl acetate/heptane.

In another embodiment, is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form of (3,5-dibromo-4-hydroxyphenyl)(2-(1-hydroxyethyl)benzofuran-3-yl-4,5,6,7-$d_4$)methanone is Form 2 having at least one of the following properties:
  (a) an X-ray powder diffraction (XRPD) pattern substantially the same as shown in FIG. 4;
  (b) an X-ray powder diffraction (XRPD) pattern with characteristic peaks at 8.3° 2-Theta, 10.7° 2-Theta, 16.6° 2-Theta, 19.7° 2-Theta, 23.7° 2-Theta, 25.0° 2-Theta, 25.6° 2-Theta, and 27.1° 2-Theta;
  (c) a thermogravimetric analysis (TGA) substantially similar to the one set forth in FIG. 5;
  (d) a DSC thermogram substantially similar to the one set forth in FIG. 6;
  (e) a DSC thermogram with an endotherm having an onset at about 139° C.;
  (f) non-hygroscopicity; or
  (g) combinations thereof.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form has an X-ray powder diffraction (XRPD) pattern substantially the same as shown in FIG. 4.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form has an X-ray powder diffraction (XRPD) pattern with characteristic peaks at 8.3° 2-Theta, 10.7° 2-Theta, 16.6° 2-Theta, 19.7° 2-Theta, 23.7° 2-Theta, 25.0° 2-Theta, 25.6° 2-Theta, and 27.1° 2-Theta.

In some embodiments is a crystalline form of (3,5-dibromo-4-hydroxyphenyl)(2-(1-hydroxyethyl)benzofuran- 3-yl-4,5,6,7-$d_4$)methanone, or solvate thereof, wherein the crystalline form has a thermogravimetric analysis (TGA) substantially similar to the one set forth in FIG. 5.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form has a DSC thermogram substantially similar to the one set forth in FIG. 6.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form has a DSC thermogram with an endotherm having an onset at about 139° C.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form is non-hygroscopic.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form is characterized as having properties: (a) an X-ray powder diffraction (XRPD) pattern substantially the same as shown in FIG. 4; (b) an X-ray powder diffraction (XRPD) pattern with characteristic peaks at 8.3° 2-Theta, 10.7° 2-Theta, 16.6° 2-Theta, 19.7° 2-Theta, 23.7° 2-Theta, 25.0° 2-Theta, 25.6° 2-Theta, and 27.1° 2-Theta; (c) a thermogravimetric analysis (TGA) substantially similar to the one set forth in FIG. 5; (d) a DSC thermogram substantially similar to the one set forth in FIG. 6; (e) a DSC thermogram with an endotherm having an onset at about 139° C.; and (f) non-hygroscopicity.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form is obtained from heptane or ethyl acetate/heptane.

In some embodiments is a crystalline form of (3,5-dibromo-4-hydroxyphenyl)(2-(1-hydroxyethyl)benzofuran-3-yl-4,5,6,7-$d_4$)methanone, wherein the crystalline form is unsolvated.

In some embodiments is a crystalline form of (3,5-dibromo-4-hydroxyphenyl)(2-(1-hydroxyethyl)benzofuran-3-yl-4,5,6,7-$d_4$)methanone, wherein the crystalline form is anhydrous.

In another embodiment, is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form of (3,5-dibromo-4-hydroxyphenyl)(2-(1-hydroxyethyl)benzofuran-3-yl-4,5,6,7-$d_4$)methanone is Form 1 having at least one of the following properties:
(a) an X-ray powder diffraction (XRPD) pattern substantially the same as shown in FIG. 7;
(b) an X-ray powder diffraction (XRPD) pattern with characteristic peaks at 5.6° 2-Theta, 11.5° 2-Theta, 13.8° 2-Theta, 14.3° 2-Theta, 17.0° 2-Theta, 18.9° 2-Theta, 27.9° 2-Theta, and 31.4° 2-Theta;
(c) a thermogravimetric analysis (TGA) substantially similar to the one set forth in FIG. 8;
(d) a DSC thermogram substantially similar to the one set forth in FIG. 9;
(e) a DSC thermogram with an endotherm having an onset at about 80° C.; or
(f) combinations thereof.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form has an X-ray powder diffraction (XRPD) pattern substantially the same as shown in FIG. 7.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form has an X-ray powder diffraction (XRPD) pattern with characteristic peaks at 5.6° 2-Theta, 11.5° 2-Theta, 13.8° 2-Theta, 14.3° 2-Theta, 17.0° 2-Theta, 18.9° 2-Theta, 27.9° 2-Theta, and 31.4° 2-Theta.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form has a thermogravimetric analysis (TGA) substantially similar to the one set forth in FIG. 8.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form has a DSC thermogram substantially similar to the one set forth in FIG. 9.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form has a DSC thermogram with an endotherm having an onset at about 80° C.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form is characterized as having properties: (a) an X-ray powder diffraction (XRPD) pattern substantially the same as shown in FIG. 7; (b) an X-ray powder diffraction (XRPD) pattern with characteristic peaks at 5.6° 2-Theta, 11.5° 2-Theta, 13.8° 2-Theta, 14.3° 2-Theta, 17.0° 2-Theta, 18.9° 2-Theta, 27.9° 2-Theta, and 31.4° 2-Theta; (c) a thermogravimetric analysis (TGA) substantially similar to the one set forth in FIG. 8; (d) a DSC thermogram substantially similar to the one set forth in FIG. 9; and (e) a DSC thermogram with an endotherm having an onset at about 80° C.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, wherein the crystalline form is obtained from methanol, ethanol, isopropanol, toluene, water, acetonitrile, heptane, acetone, tert-butyl methyl ether, 2-butanone, ethyl acetate, isopropyl acetate, tetrahydrofuran, or combinations thereof.

In some embodiments is a crystalline form of (3,5-dibromo-4-hydroxyphenyl)(2-(1-hydroxyethyl)benzofuran-3-yl-4,5,6,7-$d_4$)methanone, or solvate thereof, for use in medicine.

In some embodiments is (3,5-dibromo-4-hydroxyphenyl)(2-(1-hydroxyethyl)benzofuran-3-yl-4,5,6,7-$d_4$)methanone, wherein (3,5-dibromo-4-hydroxyphenyl)(2-(1-hydroxyethyl)benzofuran-3-yl-4,5,6,7-$d_4$)methanone is amorphous.

In another aspect, described herein is a pharmaceutical composition comprising a crystalline form of (3,5-dibromo-4-hydroxyphenyl)(2-(1-hydroxyethyl)benzofuran-3-yl-4,5,6,7-$d_4$)methanone, or solvate thereof, and at least one inactive ingredient selected from pharmaceutically acceptable carriers, diluents, and excipients.

In another aspect, described herein is a pharmaceutical composition comprising a crystalline form of (3,5-dibromo-4-hydroxyphenyl)(2-(1-hydroxyethyl)benzofuran-3-yl-4,5,6,7-$d_4$)methanone, or solvate thereof, formulated for oral, intravenous, intramuscular, or subcutaneous administration.

In another aspect, described herein is a method for treating hyperuricemia or gout in an individual in need thereof, comprising administering to the individual a therapeutically effective amount of a crystalline form of (3,5-dibromo-4-hydroxyphenyl)(2-(1-hydroxyethyl)benzofuran-3-yl-4,5,6,7-$d_4$)methanone, or solvate thereof, described herein. In some embodiments is a method for treating hyperuricemia or gout in an individual in need thereof, comprising administering to the individual a therapeutically effective amount of a crystalline form of (3,5-dibromo-4-hydroxyphenyl)(2-(1-hydroxyethyl)benzofuran-3-yl-4,5,6,7-$d_4$)methanone, or solvate thereof, described herein, wherein (3,5-dibromo-4-hydroxyphenyl)(2-(1-hydroxyethyl)benzofuran-3-yl-4,5,6,7-$d_4$)methanone is administered orally. In some embodiments is a method for treating hyperuricemia or gout in an individual in need thereof, comprising administering to the individual a therapeutically effective amount of a crystalline form of (3,5-dibromo-4-hydroxyphenyl)(2-(1-hydroxyethyl)benzofuran-3-yl-4,5,6,7-$d_4$)methanone, or solvate thereof, described herein, wherein the therapeutically effective amount is taken with food. In some embodiments is a method for treating hyperuricemia or gout in an individual in need thereof, comprising administering to the individual a therapeutically effective amount of a crystalline form of (3,5-dibromo-4-hydroxyphenyl)(2-(1-hydroxyethyl)benzofuran-3-yl-4,5,6,7-$d_4$)methanone, or solvate thereof, described herein, wherein the therapeutically effective amount is taken without food. In some embodiments is a method for treating hyperuricemia or gout in an individual in need thereof, comprising administering to the individual a therapeutically effective amount of a crystalline form of (3,5-dibromo-4-hydroxyphenyl)(2-(1-hydroxyethyl)benzofuran-3-yl-4,5,6,7-$d_4$)methanone, or solvate thereof, described herein, wherein (3,5-dibromo-4-hydroxyphenyl)(2-(1-hydroxyethyl)benzofuran-3-yl-4,5,6,7-$d_4$)methanone is administered to the individual once per day. In some embodiments is a method for treating hyperuricemia or gout in an individual in need thereof, comprising administering to the individual a therapeutically effective amount of a crystalline form of (3,5-dibromo-4-hydroxyphenyl)(2-(1-hydroxyethyl)benzofuran-3-yl-4,5,6,7-$d_4$)methanone, or solvate thereof, described herein, wherein (3,5-dibromo-4-hydroxyphenyl)(2-(1-hydroxyethyl)benzofuran-3-yl-4,5,6,7-$d_4$)methanone is administered to the individual twice per day.

In some embodiments, described herein is a method for treating hyperuricemia or gout in an individual in need thereof, comprising administering to the individual a therapeutically effective amount of a crystalline form of (3,5-dibromo-4-hydroxyphenyl)(2-(1-hydroxyethyl)benzofuran-3-yl-4,5,6,7-$d_4$)methanone, or solvate thereof, described herein, further comprising administering at least one additional therapeutic agent. In some embodiments, described herein is a method for treating hyperuricemia or gout in an individual in need thereof, comprising administering to the individual a therapeutically effective amount of a crystalline form of (3,5-dibromo-4-hydroxyphenyl)(2-(1-hydroxyethyl)benzofuran-3-yl-4,5,6,7-$d_4$)methanone, or solvate thereof, described herein, further comprising administering a xanthine oxidase inhibitor. In some embodiments, described herein is a method for treating hyperuricemia or gout in an individual in need thereof, comprising administering to the individual a therapeutically effective amount of a crystalline form of (3,5-dibromo-4-hydroxyphenyl)(2-(1-hydroxyethyl)benzofuran-3-yl-4,5,6,7-$d_4$)methanone, or solvate thereof, described herein, further comprising administering a xanthine oxidase inhibitor, wherein the xanthine oxidase inhibitor is allopurinol, oxypurinol, febuxostat, topiroxostat, or inositol. In some embodiments, described herein is a method for treating hyperuricemia or gout in an individual in need thereof, comprising administering to the individual a therapeutically effective amount of a crystalline form of (3,5-dibromo-4-hydroxyphenyl)(2-(1-hydroxyethyl)benzofuran-3-yl-4,5,6,7-$d_4$)methanone, or solvate thereof, described herein, further comprising administering a sodium-glucose co-transporter-2 (SGLT2) inhibitor. In some embodiments, described herein is a method for treating hyperuricemia or gout in an individual in need thereof, comprising administering to the individual a therapeutically effective amount of a crystalline form of (3,5-dibromo-4-hydroxyphenyl)(2-(1-hydroxyethyl)benzofuran-3-yl-4,5,6,7-$d_4$)methanone, or solvate thereof, described herein, further comprising administering an SGLT2 inhibitor, wherein the SGLT2 inhibitor is selected from canagliflozin, dapagliflozin, empagliflozin, empagliflozin/linagliptin, empagliflozin/metformin, and dapagliflozin/metformin. In some embodiments, described herein is a method for treating hyperuricemia or gout in an individual in need thereof, comprising administering to the individual a therapeutically effective amount of a crystalline form of (3,5-dibromo-4-hydroxyphenyl)(2-(1-hydroxyethyl)benzofuran-3-yl-4,5,6,7-$d_4$)methanone, or solvate thereof, described herein, further comprising administering a xanthine oxidase inhibitor and an SGLT2 inhibitor. In some embodiments, described herein is a method for treating hyperuricemia or gout in an individual in need thereof, comprising administering to the individual a therapeutically effective amount of a crystalline form of (3,5-dibromo-4-hydroxyphenyl)(2-(1-hydroxyethyl)benzofuran-3-yl-4,5,6,7-$d_4$)methanone, or solvate thereof, described herein, further comprising administering a xanthine oxidase inhibitor and an SGLT2 inhibitor, wherein the xanthine oxidase inhibitor, wherein the xanthine oxidase inhibitor is allopurinol, oxypurinol, febuxostat, topiroxostat, or inositol, and the SGLT2 inhibitor is selected from canagliflozin, dapagliflozin, empagliflozin, empagliflozin/linagliptin, empagliflozin/metformin, and dapagliflozin/metformin.

INCORPORATION BY REFERENCE

All publications, patents, and patent applications mentioned in this specification are herein incorporated by reference to the extent applicable and relevant and to the same extent as if each individual publication, patent, or patent application was specifically and individually indicated to be incorporated by reference.

DETAILED DESCRIPTION OF THE INVENTION

Figure 1:
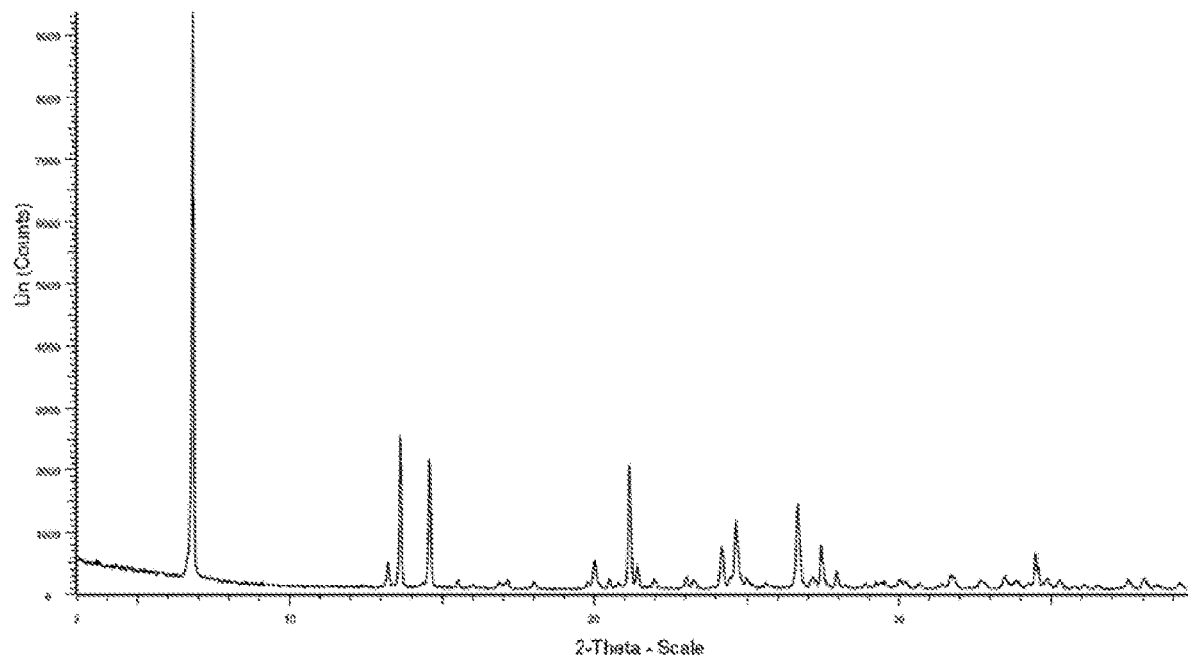
FIG. 1. Illustrates an X-ray powder diffraction (XRPD) pattern of crystalline (3,5-dibromo-4-hydroxyphenyl)(2-(1-hydroxyethyl)benzofuran-3-yl-4,5,6,7-$d_4$)methanone (Compound 1), Form 3.

Benzbromarone is a uricosuric agent effective in lowering serum uric acid sUA and treating gout. It has been found that therapy using benzbromarone can lead to lowering of sUA even following a single dose and continue to be lowered following multiple doses, and that chronic therapy can bring sUA into target levels of <6 mg/dL. However, in certain patients, benzbromarone is associated with hepatotoxicity. A high proportion of these patients developed acute liver failure leading to death or emergency liver transplantation. As a result, benzbromarone was never approved for use in the United States. In addition, the hepatotoxicity of benzbromarone led to its withdrawal in Europe in 2003. Benzbromarone is converted to reactive metabolites by CYP2C9. Benzbromarone is metabolized to 5,6-dihydroxybenzbromarone via 6-OH benzbromarone by CYP2C9, followed by the oxidation of 5,6-dihydroxybenzbromarone to a reactive ortho-quinone intermediate. The mechanism of benzbromarone hepatotoxicity is believed to be a result of its hepatic metabolism by CYP2C9 and possible effects of the 6-OH benzbromarone and its further metabolites on mitochondrial function (Iwamura et al., Drug Metabolism and Disposition, 2011, 39, 838-846; Uchida et al., Drug Metab. Pharmacokinet., 2010, 25, 605-610).

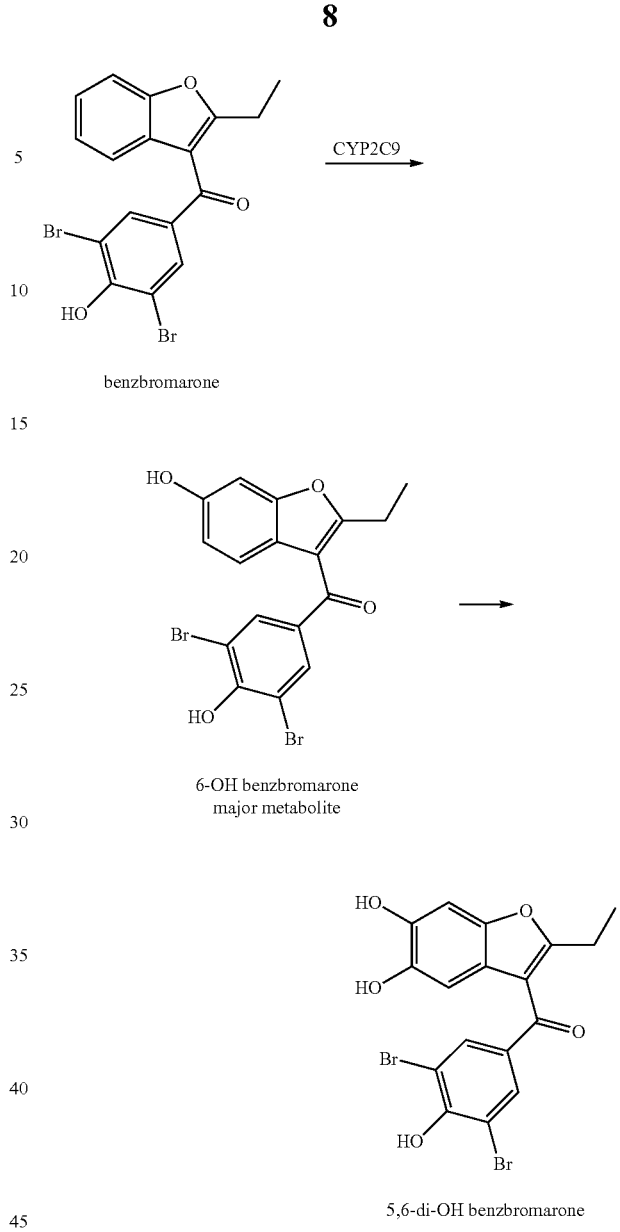

Described herein are crystalline forms of (3,5-dibromo-4-hydroxyphenyl)(2-(1-hydroxyethyl)benzofuran-3-yl-4,5,6,7-$d_4$)methanone (Compound 1), a 4,5,6,7-tertradeutero analog of benzbromarone. Compound 1 showed better in vitro URAT1 potency than benzbromarone. Compound 1 also demonstrated an improved metabolic profile compared to benzbromarone. Compound 1 is more stable than benzbromarone in human microsomes. The CYP2C9 metabolic pathway of the compound is significantly reduced and the 6-OH benzbromarone 5,6-di-OH benzbromarone metabolites are not formed. Thus, Compound 1 represents a prospective therapeutic agent for the treatment of hyperuricemia and gout with an improved hepatotoxicity profile.

Compound 1

In one embodiment is (3,5-dibromo-4-hydroxyphenyl)(2-(1-hydroxyethyl)benzofuran-3-yl-4,5,6,7-$d_4$)methanone. "Compound 1" or "(3,5-dibromo-4-hydroxyphenyl)(2-(1-hydroxyethyl)benzofuran-3-yl-4,5,6,7-$d_4$)methanone" refers to the compound with the following structure:

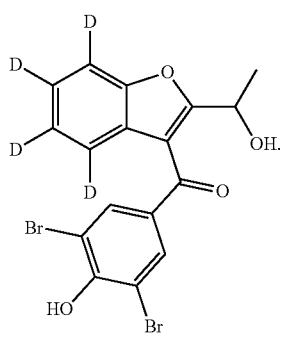 [SMILES: [2H]c1c([2H])c([2H])c2c(C(=O)c3cc(Br)c(O)c(Br)c3)c(C(C)O)oc2c1[2H]]

In some embodiments, Compound 1 includes the solvent addition forms (solvates). Solvates contain either stoichiometric or non-stoichiometric amounts of a solvent, and are formed during the process of product formation or isolation with pharmaceutically acceptable solvents such as water, ethanol, methanol, tert-butyl methyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In some embodiments, solvates are formed using, but not limited to, Class 3 solvent(s). In some embodiments, solvates are formed using, but not limited to, Class 2 solvent(s). Categories of solvents are defined in, for example, the International Conference on Harmonization of Technical Requirements for Registration of Pharmaceuticals for Human Use (ICH), "Impurities: Guidelines for Residual Solvents Q3C(R6)," (October 2016). Hydrates are formed when the solvent is water, or alcoholates are formed when the solvent is alcohol.

In other embodiments, Compound 1 is prepared in various forms, including but not limited to, an amorphous phase, crystalline forms, milled forms, and nano-particulate forms.

While not intending to be bound by any particular theory, certain solid forms are characterized by physical properties, e.g., stability, solubility, and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein.

Crystalline Forms

The identification and selection of a solid form of a pharmaceutical compound are complex, given that a change in solid form may affect a variety of physical and chemical properties, which may provide benefits or drawbacks in processing, formulation, stability, bioavailability, storage, and handling (e.g., shipping), among other important pharmaceutical characteristics. Useful pharmaceutical solids include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability.

Whether crystalline or amorphous, solid forms of a pharmaceutical compound include single-component and multiple-component solids. Single-component solids consist essentially of the pharmaceutical compound or active ingredient in the absence of other compounds. Variety among single-component crystalline materials may potentially arise from the phenomenon of polymorphism, wherein multiple three-dimensional arrangements exist for a particular pharmaceutical compound.

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*:3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (At present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," ACA Transactions 39:14-23 (a great deal still needs to be learned and done before one can state with any degree of confidence the ability to predict a crystal structure, much less polymorphic forms)).

The variety of possible solid forms creates potential diversity in physical and chemical properties for a given pharmaceutical compound. The discovery and selection of solid forms are of great importance in the development of an effective, stable, and marketable pharmaceutical product.

Crystalline Compound 1, Form 3

Figure 2:
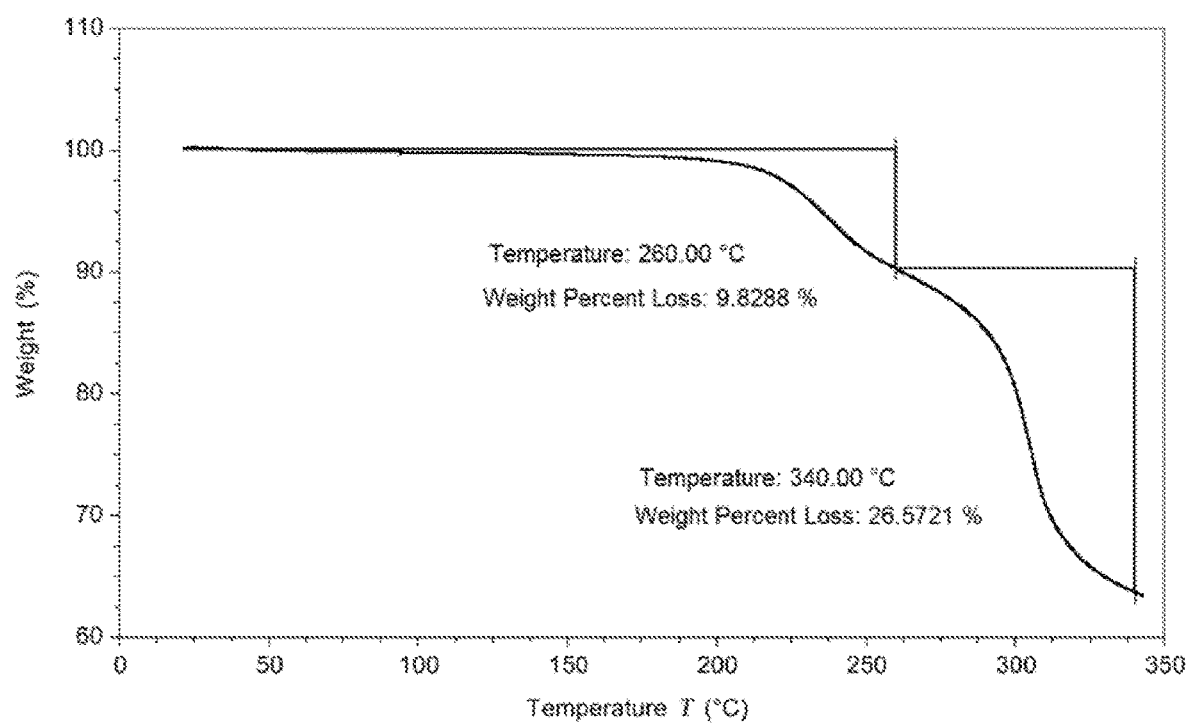
FIG. 2. Illustrates a thermogravimetric analysis (TGA) thermogram of crystalline (3,5-dibromo-4-hydroxyphenyl)(2-(1-hydroxyethyl)benzofuran-3-yl-4,5,6,7-$d_4$)methanone (Compound 1), Form 3.
Figure 3:
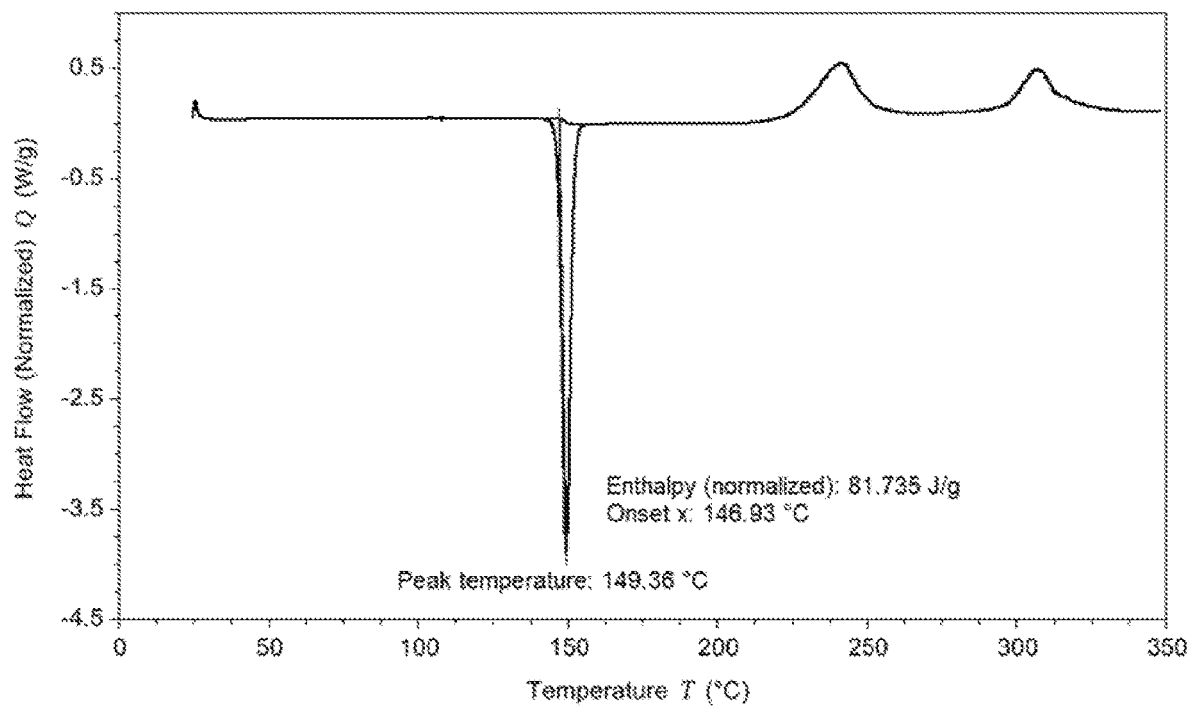
FIG. 3. Illustrates a differential scanning calorimetry (DSC) thermogram of crystalline (3,5-dibromo-4-hydroxyphenyl)(2-(1-hydroxyethyl)benzofuran-3-yl-4,5,6,7-$d_4$) methanone (Compound 1), Form 3.

In some embodiments, Compound 1 is crystalline. In some embodiments, Compound 1 is crystalline and anhydrous. In some embodiments, crystalline Compound 1 is Form 3 characterized as having at least one of the following properties:

(a) an X-ray powder diffraction (XRPD) pattern substantially the same as shown in FIG. 1;

(b) an X-ray powder diffraction (XRPD) pattern with characteristic peaks at 6.8° 2-Theta, 13.6° 2-Theta, 14.6° 2-Theta, 21.2° 2-Theta, 24.2° 2-Theta, 24.7° 2-Theta, 26.7° 2-Theta, and 27.5° 2-Theta;

(c) a thermogravimetric analysis (TGA) substantially similar to the one set forth in FIG. 2;

(d) a DSC thermogram substantially similar to the one set forth in FIG. 3;

(e) a DSC thermogram with an endotherm having an onset at about 147° C.;

(f) non-hygroscopicity; or (g) combinations thereof.

In some embodiments, crystalline Compound 1, Form 3, is characterized as having at least two of the properties selected from (a) to (f). In some embodiments, crystalline Compound 1, Form 3, is characterized as having at least three of the properties selected from (a) to (f). In some embodiments, crystalline Compound 1, Form 3, is characterized as having at least four of the properties selected from (a) to (f). In some embodiments, crystalline Compound 1, Form 3, is characterized as having at least five of the properties selected from (a) to (f). In some embodiments, crystalline Compound 1, Form 3, is characterized as having properties (a) to (f).

In some embodiments, crystalline Compound 1, Form 3, has an X-ray powder diffraction (XRPD) pattern substantially the same as shown in FIG. 1. In some embodiments, crystalline Compound 1, Form 3, has an X-ray powder diffraction (XRPD) pattern with characteristic peaks at 6.8° 2-Theta, 13.6° 2-Theta, 14.6° 2-Theta, 21.2° 2-Theta, 24.2° 2-Theta, 24.7° 2-Theta, 26.7° 2-Theta, and 27.5° 2-Theta. In some embodiments, crystalline Compound 1, Form 3, has a thermogravimetric analysis (TGA) thermogram substantially similar to the one set forth in FIG. 2. In some embodiments, crystalline Compound 1, Form 3, has a DSC thermogram substantially similar to the one set forth in FIG. 3. In some embodiments, crystalline Compound 1, Form 3, has a DSC thermogram with an endotherm having an onset at about 147° C. In some embodiments, crystalline Compound 1, Form 3, is non-hygroscopic. In some embodiments, crystalline Compound 1, Form 3, is obtained from toluene, toluene/heptane, or ethyl acetate/heptane. In some embodiments, crystalline Compound 1, Form 3, is obtained from toluene. In some embodiments, crystalline Compound 1, Form 3, is obtained from toluene/heptane. In some embodiments, crystalline Compound 1, Form 3, is obtained from ethyl acetate/heptane. In some embodiments, crystalline Compound 1, Form 3, is solvated. In some embodiments, crystalline Compound 1, Form 3, is unsolvated.

Crystalline Compound 1, Form 2

Figure 4:
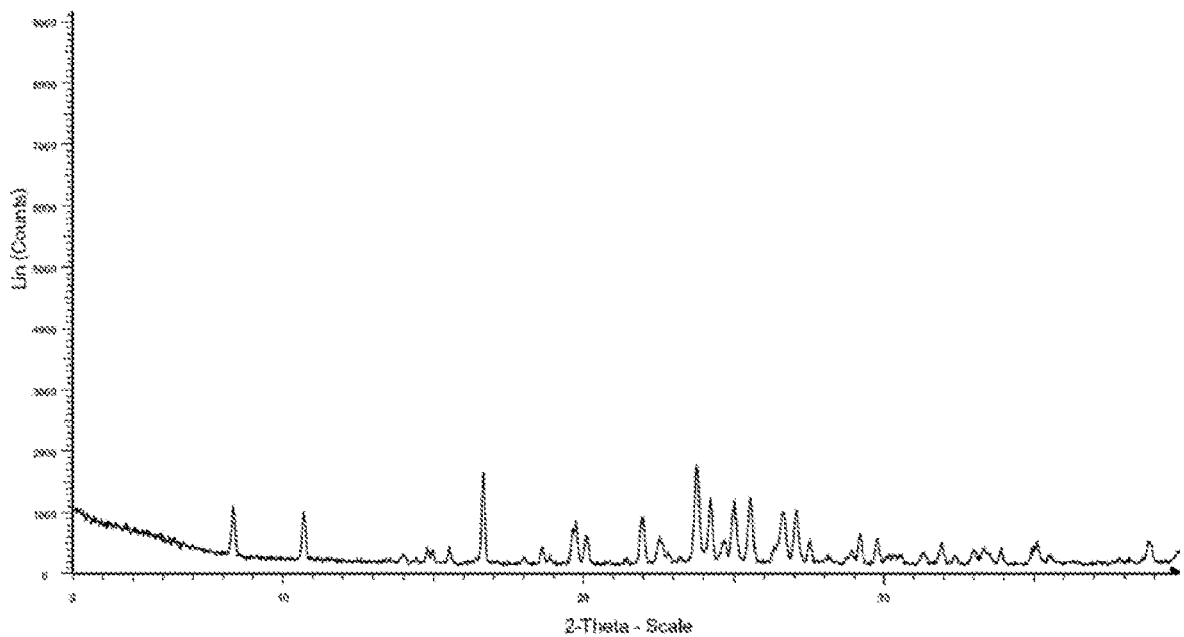
FIG. 4. Illustrates an X-ray powder diffraction (XRPD) pattern of crystalline (3,5-dibromo-4-hydroxyphenyl)(2-(1-hydroxyethyl)benzofuran-3-yl-4,5,6,7-$d_4$)methanone (Compound 1), Form 2.
Figure 5:
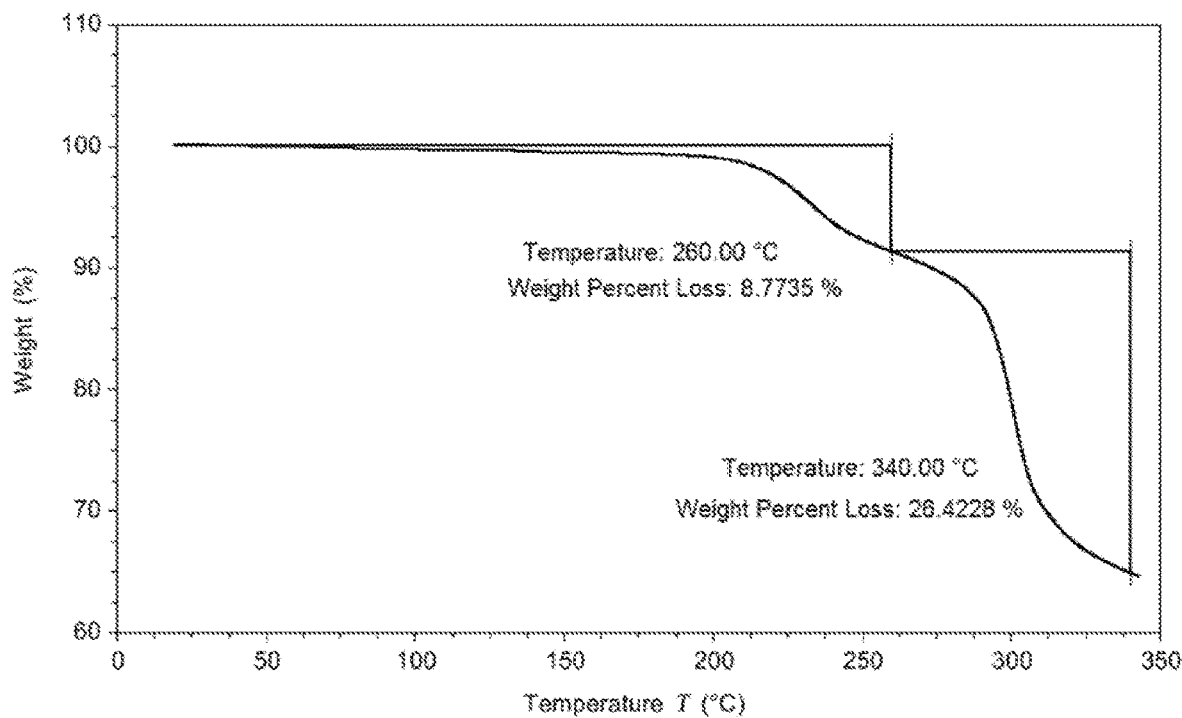
FIG. 5. Illustrates a thermogravimetric analysis (TGA) thermogram of crystalline (3,5-dibromo-4-hydroxyphenyl)(2-(1-hydroxyethyl)benzofuran-3-yl-4,5,6,7-$d_4$)methanone (Compound 1), Form 2.
Figure 6:
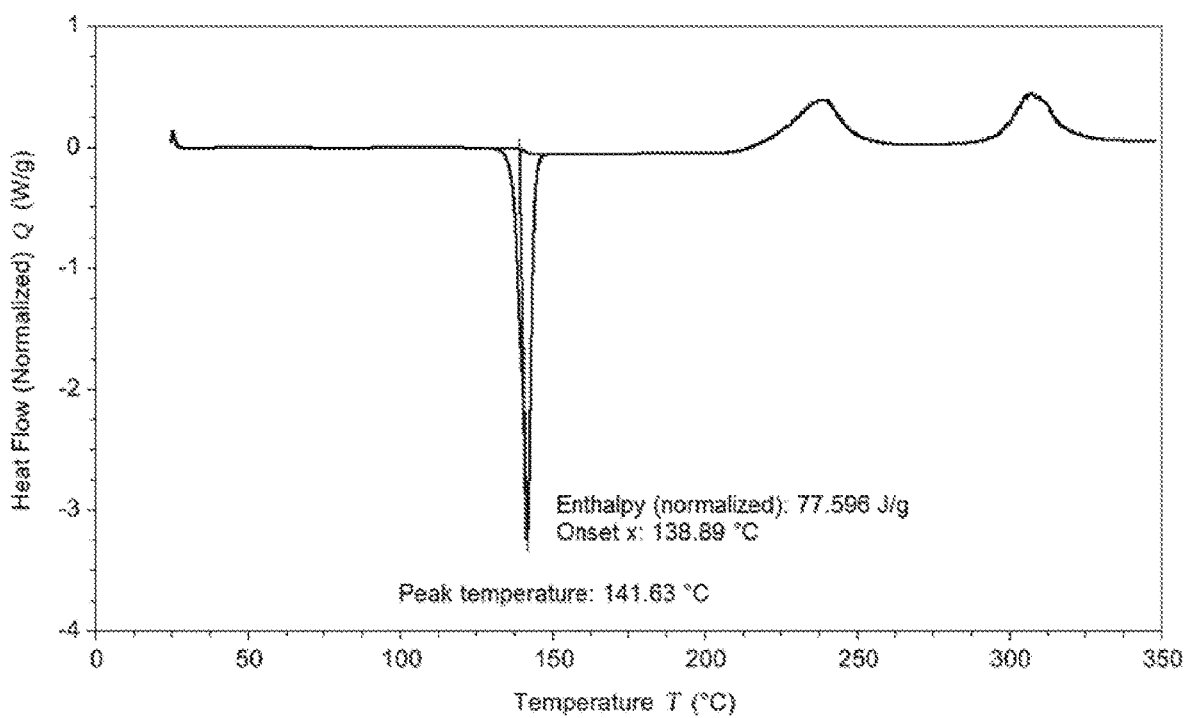
FIG. 6. Illustrates a differential scanning calorimetry (DSC) thermogram of crystalline (3,5-dibromo-4-hydroxyphenyl)(2-(1-hydroxyethyl)benzofuran-3-yl-4,5,6,7-$d_4$)methanone (Compound 1), Form 2.

In some embodiments, crystalline Compound 1 is Form 2 characterized as having at least one of the following properties:
  (a) an X-ray powder diffraction (XRPD) pattern substantially the same as shown in FIG. 4;
  (b) an X-ray powder diffraction (XRPD) pattern with characteristic peaks at 8.3° 2-Theta, 10.7° 2-Theta, 16.6° 2-Theta, 19.7° 2-Theta, 23.7° 2-Theta, 25.0° 2-Theta, 25.6° 2-Theta, and 27.1° 2-Theta;
  (c) a thermogravimetric analysis (TGA) substantially similar to the one set forth in FIG. 5;
  (d) a DSC thermogram substantially similar to the one set forth in FIG. 6;
  (e) a DSC thermogram with an endotherm having an onset at about 139° C.;
  (f) non-hygroscopicity; or
  (g) combinations thereof.

In some embodiments, crystalline Compound 1, Form 2, is characterized as having at least two of the properties selected from (a) to (f). In some embodiments, crystalline Compound 1, Form 2, is characterized as having at least three of the properties selected from (a) to (f). In some embodiments, crystalline Compound 1, Form 2, is characterized as having at least four of the properties selected from (a) to (f). In some embodiments, crystalline Compound 1, Form 2, is characterized as having at least five of the properties selected from (a) to (f). In some embodiments, crystalline Compound 1, Form 2, is characterized as having properties (a) to (f).

In some embodiments, crystalline Compound 1, Form 2, has an X-ray powder diffraction (XRPD) pattern substantially the same as shown in FIG. 4. In some embodiments, crystalline Compound 1, Form 2, has an X-ray powder diffraction (XRPD) pattern with characteristic peaks at 8.3° 2-Theta, 10.7° 2-Theta, 16.6° 2-Theta, 19.7° 2-Theta, 23.7° 2-Theta, 25.0° 2-Theta, 25.6° 2-Theta, and 27.1° 2-Theta. In some embodiments, crystalline Compound 1, Form 2, has a thermogravimetric analysis (TGA) thermogram substantially similar to the one set forth in FIG. 5. In some embodiments, crystalline Compound 1, Form 2, has a DSC thermogram substantially similar to the one set forth in FIG. 6. In some embodiments, crystalline Compound 1, Form 2, has a DSC thermogram with an endotherm having an onset at about 139° C. In some embodiments, crystalline Compound 1, Form 2, is non-hygroscopic. In some embodiments, crystalline Compound 1, Form 2, is obtained from toluene, toluene/heptane, or ethyl acetate/heptane. In some embodiments, crystalline Compound 1, Form 2, is obtained from toluene. In some embodiments, crystalline Compound 1, Form 2, is obtained from toluene/heptane. In some embodiments, crystalline Compound 1, Form 2, is obtained from ethyl acetate/heptane. In some embodiments, crystalline Compound 1, Form 2, is solvated. In some embodiments, crystalline Compound 1, Form 2, is unsolvated.

Crystalline Compound 1, Form 1

Figure 7:
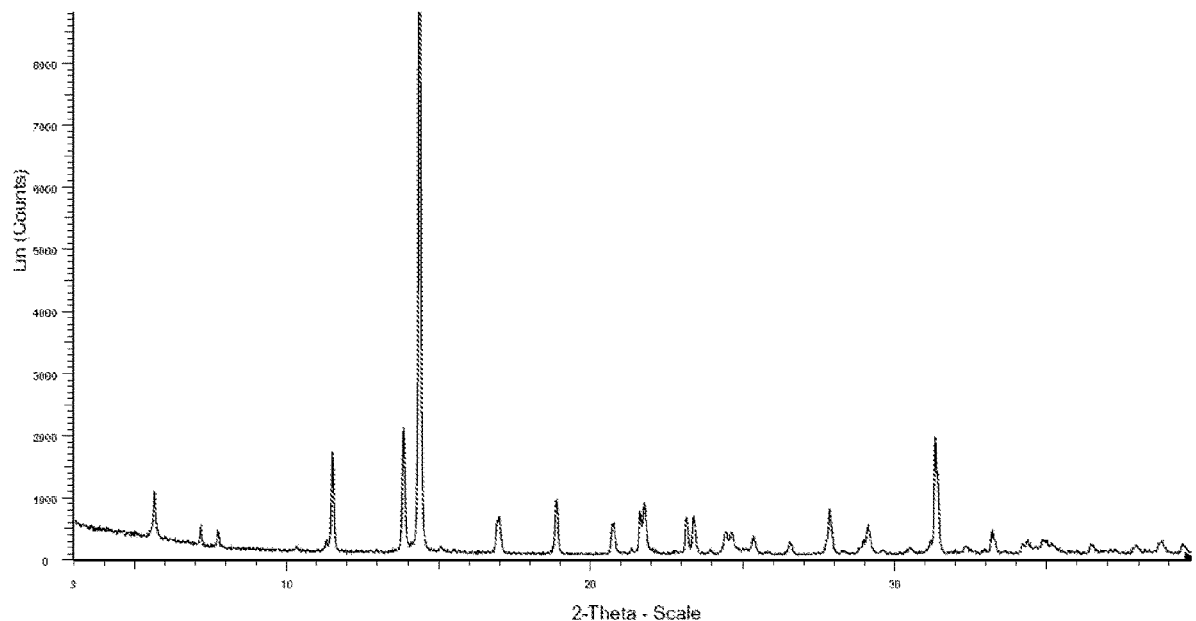
FIG. 7. Illustrates an X-ray powder diffraction (XRPD) pattern of crystalline (3,5-dibromo-4-hydroxyphenyl)(2-(1-hydroxyethyl)benzofuran-3-yl-4,5,6,7-$d_4$)methanone (Compound 1), Form 1.
Figure 8:
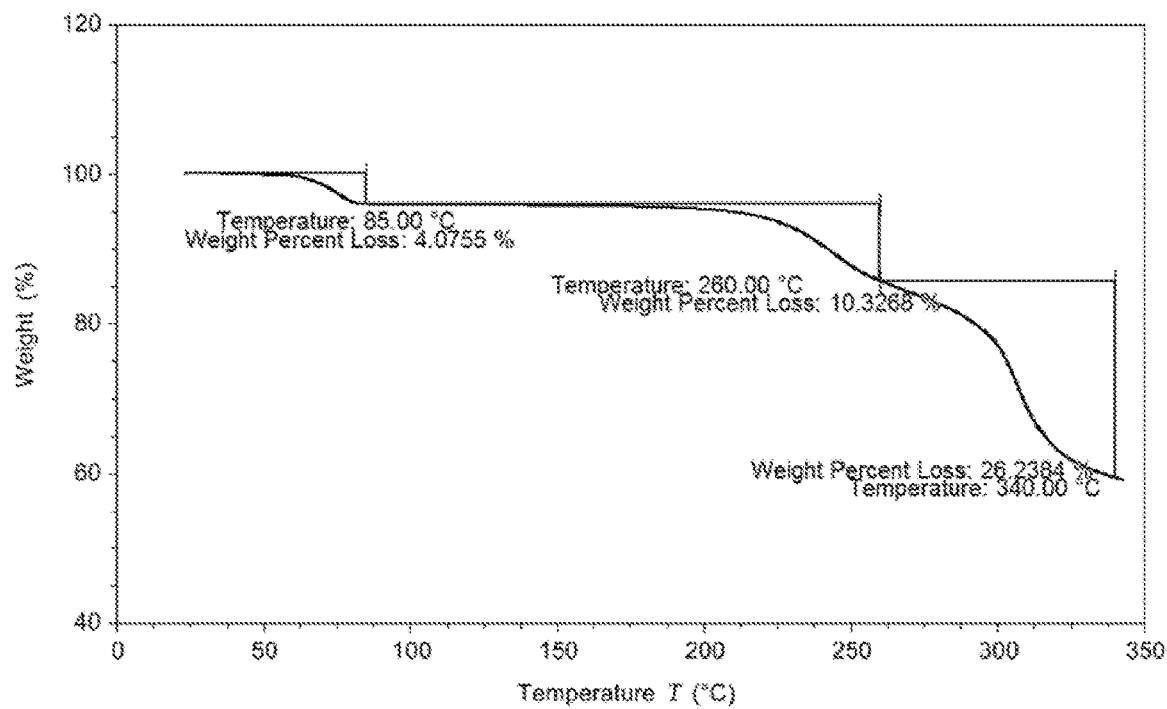
FIG. 8. Illustrates a thermogravimetric analysis (TGA) thermogram of crystalline (3,5-dibromo-4-hydroxyphenyl)(2-(1-hydroxyethyl)benzofuran-3-yl-4,5,6,7-$d_4$)methanone (Compound 1), Form 1.
Figure 9:
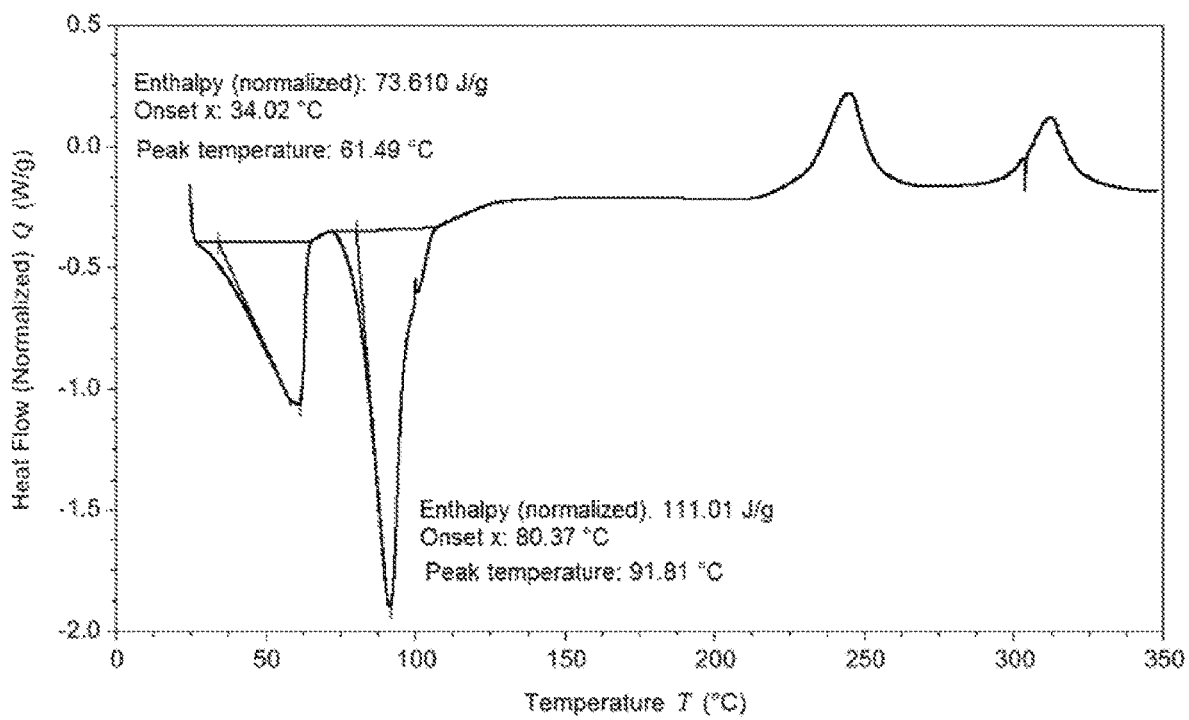
FIG. 9. Illustrates a differential scanning calorimetry (DSC) thermogram of crystalline (3,5-dibromo-4-hydroxyphenyl)(2-(1-hydroxyethyl)benzofuran-3-yl-4,5,6,7-$d_4$)methanone (Compound 1), Form 1.

In some embodiments, crystalline Compound 1 is Form 1 characterized as having at least one of the following properties:
  (a) an X-ray powder diffraction (XRPD) pattern substantially the same as shown in FIG. 7;
  (b) an X-ray powder diffraction (XRPD) pattern with characteristic peaks at 5.6° 2-Theta, 11.5° 2-Theta, 13.8° 2-Theta, 14.3° 2-Theta, 17.0° 2-Theta, 18.9° 2-Theta, 27.9° 2-Theta, and 31.4° 2-Theta;
  (c) a thermogravimetric analysis (TGA) substantially similar to the one set forth in FIG. 8;
  (d) a DSC thermogram substantially similar to the one set forth in FIG. 9;
  (e) a DSC thermogram with an endotherm having an onset at about 80° C.; or
  (f) combinations thereof.

In some embodiments, crystalline Compound 1, Form 1, is characterized as having at least two of the properties selected from (a) to (e). In some embodiments, crystalline Compound 1, Form 1, is characterized as having at least three of the properties selected from (a) to (e). In some embodiments, crystalline Compound 1, Form 1, is characterized as having at least four of the properties selected from (a) to (e). In some embodiments, crystalline Compound 1, Form 1, is characterized as having properties (a) to (e).

In some embodiments, crystalline Compound 1, Form 1, has an X-ray powder diffraction (XRPD) pattern substantially the same as shown in FIG. 7. In some embodiments, crystalline Compound 1, Form 1, has an X-ray powder diffraction (XRPD) pattern with characteristic peaks at 5.6° 2-Theta, 11.5° 2-Theta, 13.8° 2-Theta, 14.3° 2-Theta, 17.0° 2-Theta, 18.9° 2-Theta, 27.9° 2-Theta, and 31.4° 2-Theta. In some embodiments, crystalline Compound 1, Form 1, has a thermogravimetric analysis (TGA) thermogram substantially similar to the one set forth in FIG. 8. In some embodiments, crystalline Compound 1, Form 1, has a DSC thermogram substantially similar to the one set forth in FIG. 9. In some embodiments, crystalline Compound 1, Form 1, has a DSC thermogram with an endotherm having an onset at about 80° C. In some embodiments, crystalline Compound 1, Form 1, is non-hygroscopic. In some embodiments, crystalline Compound 1, Form 1, is obtained from toluene, toluene/heptane, or ethyl acetate/heptane. In some embodiments, crystalline Compound 1, Form 1, is obtained from toluene. In some embodiments, crystalline Compound 1, Form 1, is obtained from toluene/heptane. In some embodiments, crystalline Compound 1, Form 1, is obtained from ethyl acetate/heptane. In some embodiments, crystalline Compound 1, Form 1, is solvated. In some embodiments, crystalline Compound 1, Form 1, is unsolvated.

Preparation of Crystalline Compound 1

In some embodiments, crystalline forms of Compound 1 are prepared as outlined in the Examples. It is noted that solvents, temperatures and other reaction conditions presented herein may vary.

In certain embodiments, provided herein are methods for making a solid form of Compound 1, comprising 1) obtaining a saturated solution of Compound 1 in a solvent at a first temperature (e.g., about 50° C.); 2) adding an anti-solvent into the saturated solution at the first temperature; 3) cooling down to a second temperature (e.g., about −5° C. to room temperature); and 4) collecting a solid if there is precipitation, and evaporating the solvent to collect a solid if there is no precipitation; and 5) optionally drying. In certain embodiments, provided herein are methods for making a solid form of Compound 1, comprising 1) obtaining a saturated solution of Compound 1 in a solvent at about 50° C.; 2) adding an anti-solvent into the saturated solution at about 50° C.; 3) cooling down to about room temperature; and 4) collecting a solid if there is precipitation, and evaporating the solvent to collect a solid if there is no precipitation; and 5) optionally air drying. In certain embodiments, the ratio by volume of solvent and anti-solvent is about 1:9. In certain embodiments, the ratio by volume of solvent and anti-solvent is about 1:4. In certain embodiments, the ratio by volume of solvent and anti-solvent is about 1:2. In certain embodiments, the ratio by volume of solvent and anti-solvent is about 1:1. In certain embodiments, the methods for making a solid form of Compound 1 are anti-solvent recrystallization experiments.

In another embodiment, crystalline Compound 1, Form 3, is substantially pure. In certain embodiments, the substantially pure crystalline Compound 1, Form 3, is substantially free of other solid forms, e.g., amorphous solid. In certain embodiments, the purity of the substantially pure crystalline Compound 1, Form 3, is no less than about 95%, no less than about 96%, no less than about 97%, no less than about 98%, no less than about 98.5%, no less than about 99%, no less than about 99.5%, or no less than about 99.8%.

In another embodiment, crystalline Compound 1, Form 2, is substantially pure. In certain embodiments, the substantially pure crystalline Compound 1, Form 2, is substantially free of other solid forms, e.g., amorphous solid. In certain embodiments, the purity of the substantially pure crystalline Compound 1, Form 2, is no less than about 95%, no less than about 96%, no less than about 97%, no less than about 98%, no less than about 98.5%, no less than about 99%, no less than about 99.5%, or no less than about 99.8%.

In another embodiment, crystalline Compound 1, Form 1, is substantially pure. In certain embodiments, the substantially pure crystalline Compound 1, Form 1, is substantially free of other solid forms, e.g., amorphous solid. In certain embodiments, the purity of the substantially pure crystalline Compound 1, Form 1, is no less than about 95%, no less than about 96%, no less than about 97%, no less than about 98%, no less than about 98.5%, no less than about 99%, no less than about 99.5%, or no less than about 99.8%.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. In some embodiments, solvents disclosed herein are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents Q3C(R6)," (October 2016).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cumene, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene and xylene.

Class 3 solvents, which possess low toxicity, include: acetic acid, acetone, anisole, 1-butanol, 2-butanol, butyl acetate, tert-butyl methyl ether (MTBE), dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, pentane, 1-pentanol, 1-propanol, 2-propanol, propyl acetate, and triethylamine.

Residual solvents in active pharmaceutical ingredients (APIs) originate from the manufacture of APIs. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising Compound 1 comprise an organic solvent(s). In some embodiments, compositions comprising Compound 1 comprise a residual amount of an organic solvent(s). In some embodiments, compositions comprising Compound 1 comprise a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butyl methyl ether (MTBE), dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, pentane, 1-pentanol, 1-propanol, 2-propanol, propyl acetate, and triethylamine. In some embodiments, the Class 3 solvent is selected from the group consisting of acetone, ethyl acetate, isopropyl acetate, tert-butyl methyl ether, heptane, isopropanol, and ethanol.

In some embodiments, compositions comprising Compound 1 comprise a residual amount of a Class 2 solvent. In some embodiments, the organic solvent is a Class 2 solvent. In some embodiments, the Class 2 solvent is selected from the group consisting of acetonitrile, chlorobenzene, chloroform, cumene, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethylene glycol, formamide, hexane, methanol, 2-methoxyethanol, methylbutyl ketone, methylcyclohexane, methylisobutylketone, N-methylpyrrolidone, nitromethane, pyridine, sulfolane, tetrahydrofuran, tetralin, toluene, 1,1,2-trichloroethene and xylene. In some embodiments, the Class 2 solvent is selected from the group consisting of acetonitrile, tetrahydrofuran, and toluene. In some embodiments, the Class 2 solvent is acetonitrile.

In some embodiments, compositions comprising Compound 1 comprise a residual amount of a solvent for which no adequate toxicological data were found. In some embodiments, the organic solvent is a solvent for which no adequate toxicological data were found. In some embodiments, the solvent is selected from the group consisting of 2-butanone and 2-methyltetrahydrofuran.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features. The term "about" when referring to a number or a numerical range means that the number or numerical range referred to is an approximation within experimental variability (or within statistical experimental error), and thus the number or numerical range may vary between 1% and 15% of the stated number or numerical range.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, "amelioration" of the symptoms of a particular disease, disorder, or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of Compound 1 dosed that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which Compound 1 is absorbed into the general circulation when the pharmaceutical composition is taken orally as compared to intravenous injection.

"Blood plasma concentration" refers to the concentration of Compound 1 in the plasma component of blood of a subject. It is understood that the plasma concentration of Compound 1 may vary significantly between subjects, due to variability with respect to metabolism and/or possible interactions with other therapeutic agents. In accordance with one embodiment disclosed herein, the blood plasma concentration of Compound 1 may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of Compound 1 may vary from subject to subject.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of Compound 1, age, weight, general condition of the subject, the condition being treated, the severity of the condition being treated, and the judgment of the prescribing physician. By way of example only, therapeutically effective amounts may be determined by a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder, or condition. An "enhancing-effective amount," as used herein, refers to an amount adequate to enhance the effect of a therapeutic agent in the treatment of a disease, disorder, or condition. When used in a patient, amounts effective for this use will depend on the severity and course of the disease, disorder, or condition, previous therapy, the patient's health status and response to the drugs, and the judgment of the treating physician.

The term "prophylactically effective amount," as used herein, refers that amount of a composition applied to a patient which will relieve to some extent one or more of the symptoms of a disease, condition or disorder being treated. In such prophylactic applications, such amounts may depend on the patient's state of health, weight, and the like. As an example, one can determine such prophylactically effective amounts by a dose escalation clinical trial.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, $IC_{50}$ refers to a dosage, concentration or amount of a particular test compound that elicits a dose-dependent response at 50% of maximal expression of a particular response that is induced, provoked or potentiated by the particular test compound.

Pharmaceutical Compositions/Formulations

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pennsylvania 1975; Liberman, H. A. and Lachman, L., Eds., *Pharmaceutical Dosage Forms*, Marcel Decker, New York, N.Y., 1980; and *Pharmaceutical Dosage Forms and Drug Delivery* Systems, Seventh Ed. (Lippincott Williams & Wilkins1999), herein incorporated by reference in their entirety.

A pharmaceutical composition, as used herein, refers to a mixture of (3,5-dibromo-4-hydroxyphenyl)(2-(1-hydroxyethyl)benzofuran-3-yl-4,5,6,7-$d_4$)methanone (Compound 1) with other chemical components, such as carriers, stabilizers, diluents, dispersing agents, suspending agents, thickening agents, and/or excipients. The pharmaceutical composition facilitates administration of the compound to a mammal. In practicing the methods of treatment or use provided herein, therapeutically effective amounts of Compound 1 are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

In some embodiments is a pharmaceutical composition comprising (3,5-dibromo-4-hydroxyphenyl)(2-(1-hydroxyethyl)benzofuran-3-yl-4,5,6,7-$d_4$)methanone (Compound 1), and at least one inactive ingredient selected from pharmaceutically acceptable carriers, diluents, and excipients. In some embodiments is a pharmaceutical composition comprising a crystalline form of Compound 1, and at least one inactive ingredient selected from pharmaceutically acceptable carriers, diluents, and excipients. In some embodiments is a pharmaceutical composition comprising a crystalline form of Compound 1, Form 3, and at least one inactive ingredient selected from pharmaceutically acceptable carriers, diluents, and excipients. In some embodiments is a pharmaceutical composition comprising a crystalline form of Compound 1, Form 2, and at least one inactive ingredient selected from pharmaceutically acceptable carriers, diluents, and excipients. In some embodiments is a pharmaceutical composition comprising a crystalline form of Compound 1, Form 1, and at least one inactive ingredient selected from pharmaceutically acceptable carriers, diluents, and excipients.

The term "pharmaceutical combination" as used herein, means a product that results from the mixing or combining of more than one active ingredient and includes both fixed and non-fixed combinations of the active ingredients. The term "fixed combination" means that the active ingredients, e.g. Compound 1, and a co-agent, are both administered to a patient simultaneously in the form of a single entity or dosage. The term "non-fixed combination" means that the active ingredients, e.g. Compound 1, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

Dosage Forms

The pharmaceutical compositions described herein can be formulated for administration to a mammal via any conventional means including, but not limited to, oral, parenteral (e.g., intravenous, subcutaneous, or intramuscular), buccal, intranasal, rectal, or transdermal administration routes. As used herein, the term "subject" or "individual" is used to mean an animal, preferably a mammal, including a human or non-human. The terms individual, patient and subject may be used interchangeably.

Moreover, the pharmaceutical compositions described herein, which include Compound 1 can be formulated into any suitable dosage form, including but not limited to, solid oral dosage forms, controlled release formulations, fast melt formulations, effervescent formulations, tablets, powders, pills, capsules, delayed release formulations, extended release formulations, pulsatile release formulations, multiparticulate formulations, and mixed immediate release and controlled release formulations.

Pharmaceutical preparations for oral use can be obtained by mixing one or more solid excipients with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of Compound 1 with one or more pharmaceutical excipients to form a bulk blend composition. When referring to these bulk blend compositions as homogeneous, it is meant that the particles of Compound 1 are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include Compound 1, and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences,* 20th Edition (2000), a film coating is provided around the formulation of Compound 1. In one embodiment, some or all of the particles of the Compound 1 are coated. In another embodiment, some or all of the particles of the Compound 1 are microencapsulated. In still another embodiment, the particles of the Compound 1 are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol, and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the Compound 1 from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like. In some embodiments provided herein, the disintegrating agent is selected from the group consisting of natural starch, a pregelatinized starch, a sodium starch, methyl crystalline cellulose, methylcellulose, croscarmellose, croscarmellose sodium, cross-linked sodium carboxymethylcellulose, cross-linked carboxymethylcellulose, cross-linked croscarmellose, cross-linked starch such as sodium starch glycolate, cross-linked polymer such as crospovidone, cross-linked polyvinylpyrrolidone, sodium alginate, a clay, or a gum. In some embodiments provided herein, the disintegrating agent is croscarmellose sodium.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as calcium, magnesium, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like. In some embodiments provided herein, the lubricant is selected from the group consisting of stearic acid, calcium hydroxide, talc, corn starch, sodium stearyl fumarate, stearic acid, sodium stearates, magnesium stearate, zinc stearate, and waxes. In some embodiments provided herein, the lubricant is magnesium stearate.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like. In some embodiments provided herein, the diluent is selected from the group consisting of lactose, sucrose, dextrose, dextrates, maltodextrin, mannitol, xylitol, sorbitol, cyclodextrins, calcium phosphate, calcium sulfate, starches, modified starches, microcrystalline cellulose, microcellulose, and talc. In some emboidments provided herein, the diluent is microcrystalline cellulose.

The term "non water-soluble diluent" represents compounds typically used in the formulation of pharmaceuticals, such as calcium phosphate, calcium sulfate, starches, modified starches, microcrystalline cellulose, microcellulose (e.g., having a density of about 0.45 $g/cm^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10°), sodium oleate, sodium lauryl sulfate, magnesium stearate, sodium docusate, triacetin, vitamin E TPGS, and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. In some embodiments provided herein, the surfactant is selected from the group consisting of sodium lauryl sulfate, sorbitan monooleate, polyoxyethylene sorbitan monooleate, polysorbates, polaxomers, bile salts, glyceryl monostearate, copolymers of ethylene oxide and propylene oxide. In some embodiments provided herein, the surfactant is sodium lauryl sulfate.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone, and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of Compound 1 from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of Compound 1 inside of a capsule. In some embodiments, the formulations (non-aqueous suspensions and solutions) are placed in a soft gelatin capsule. In some embodiments, the formulations (non-aqueous suspensions and solutions) are placed in a hard shell gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of Compound 1 and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with Compound 1 which sufficiently isolate the Compound 1 from other non-compatible excipients. Materials compatible with Compound 1 are those that delay the release of the compounds of Compound 1 in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG,HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat JR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated Compound 1 may be formulated by several methods, illustrative examples of which include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In one embodiment, the particles of Compound 1 are microencapsulated prior to being formulated into one of the above forms. In still another embodiment, some or most of the particles are coated prior to being further formulated by using standard coating procedures, such as those described in Remington's Pharmaceutical Sciences, 20th Edition (2000).

In other embodiments, the solid dosage formulations of the Compound 1 are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with Compound 1 may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

Shellac, also called purified lac, a refined product obtained from the resinous secretion of an insect. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in the stomach and dissolve in the intestine;

Cellulose Derivatives. Examples of suitable cellulose derivatives are ethyl cellulose; and reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles<1 µm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-555, or HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions; Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include Compound 1 are delivered using a pulsatile dosage form. A pulsatile dosage form is capable of providing one or more immediate release pulses at predetermined time points after a controlled lag time or at specific sites. Other types of controlled release systems may be used. Examples of such delivery systems include, e.g., polymer-based systems, such as polylactic and polyglycolic acid, polyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms*, 2 Ed., Vol. 1, pp. 209-214 (1990); Singh et al., *Encyclopedia of Pharmaceutical Tech-* nology, 2$^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference.

In some embodiments, pharmaceutical formulations are provided that include particles of Compound 1 and at least one dispersing agent or suspending agent for oral administration to a subject. The formulations may be a powder and/or granules for suspension and, upon admixture with water, a substantially uniform suspension is obtained.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Methods

In some embodiments is a method for treating hyperuricemia or gout comprising administering to the individual in need thereof a therapeutically effective amount of a crystalline form of Compound 1 described herein. In some embodiments is a method for treating hyperuricemia comprising administering to the individual in need thereof a therapeutically effective amount of a crystalline form of Compound 1 described herein. In some embodiments is a method for treating gout comprising administering to the individual in need thereof a therapeutically effective amount of a crystalline form of Compound 1 described herein. In some embodiments is a method for treating hyperuricemia or gout comprising administering to the individual in need thereof a therapeutically effective amount of crystalline Compound 1, Form 3, described herein. In some embodiments is a method for treating hyperuricemia comprising administering to the individual in need thereof a therapeutically effective amount of crystalline Compound 1, Form 3, described herein. In some embodiments is a method for treating gout comprising administering to the individual in need thereof a therapeutically effective amount of crystalline Compound 1, Form 3, described herein. In some embodiments is a method for treating hyperuricemia or gout comprising administering to the individual in need thereof a therapeutically effective amount of crystalline Compound 1, Form 2, described herein. In some embodiments is a method for treating hyperuricemia comprising administering to the individual in need thereof a therapeutically effective amount of crystalline Compound 1, Form 2, described herein. In some embodiments is a method for treating gout comprising administering to the individual in need thereof a therapeutically effective amount of crystalline Compound 1, Form 2, described herein. In some embodiments is a method for treating hyperuricemia or gout comprising administering to the individual in need thereof a therapeutically effective amount of crystalline Compound 1, Form 1, described herein. In some embodiments is a method for treating hyperuricemia comprising administering to the individual in need thereof a therapeutically effective amount of crystalline Compound 1, Form 1, described herein. In some embodiments is a method for treating gout comprising administering to the individual in need thereof a therapeutically effective amount of crystalline Compound 1, Form 1, described herein.

Methods of Dosing and Treatment Regimens

In some embodiments, crystalline Compound 1 is used in the preparation of medicaments for the treatment of diseases or conditions that would benefit from lowering serum uric acid (sUA). In addition, a method for treating any of the diseases or conditions described herein in an individual in need of such treatment, involves administration of pharmaceutical compositions containing crystalline Compound 1, or pharmaceutically acceptable solvate thereof, in therapeutically effective amounts to said individual.

In some embodiments, compositions containing crystalline Compound 1 are administered for prophylactic, therapeutic, or maintenance treatment. In some embodiments, compositions containing Compound 1 are administered for therapeutic applications. In some embodiments, compositions containing Compound 1 are administered for prophylactic applications.

In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder, or condition, previous therapy, the patient's health status and response to the drugs, and the judgment of the treating physician.

In some embodiments, crystalline Compound 1 is administered daily. In some embodiments, crystalline Compound 1 is administered every other day.

In some embodiments, crystalline Compound 1 is administered once per day. In some embodiments, crystalline Compound 1 is administered twice per day. In some embodiments, crystalline Compound 1 is administered three times per day. In some embodiments, crystalline Compound 1 is administered four times per day.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered, if necessary. Subsequently, the dosage or the frequency of administration, or both, can be reduced, as a function of the symptoms, to a level at which the improved disease, disorder, or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, in some embodiments, about 1-about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds described herein are from about 0.01 mg/kg to about 20 mg/kg. In one embodiment, the daily dosages are from about 0.1 mg/kg to about 10 mg/kg. An indicated daily dosage in the larger mammal, including, but not limited to, humans, is in the range from about 0.5 mg to about 1000 mg, conveniently administered in a single dose or in divided doses, including, but not limited to, up to four times a day or in extended release form. Suitable unit dosage forms for oral administration include from about 1 to about 500 mg active ingredient. In one embodiment, the unit dosage is about 1 mg, about 5 mg, about, 10 mg, about 20 mg, about 50 mg, about 100 mg, about 200 mg, about 250 mg, about 400 mg, or about 500 mg. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

Compound 1 described herein, and compositions thereof, may also be used in combination with other therapeutic agents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

In certain instances, it may be appropriate to administer crystalline Compound 1 described herein in combination with another therapeutic agent. By way of example only, if one of the side effects experienced by a patient upon receiving one of the compounds herein, such as crystalline Compound 1, is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder, or condition being treated, the overall benefit experienced by the patient may simply be additive of the two therapeutic agents or the patient may experience a synergistic benefit.

In some embodiments, crystalline Compound 1 is administered in combination with a xanthine oxidase inhibitor. In some embodiments, crystalline Compound 1 is administered in combination with a xanthine oxidase inhibitor, wherein the xanthine oxidase inhibitor is allopurinol, oxypurinol, febuxostat, topiroxostat, or inositol. In some embodiments, crystalline Compound 1 is administered in combination with a xanthine oxidase inhibitor, wherein the xanthine oxidase inhibitor is allopurinol. In some embodiments, crystalline Compound 1 is administered in combination with a xanthine oxidase inhibitor, wherein the xanthine oxidase inhibitor is oxypurinol. In some embodiments, crystalline Compound 1 is administered in combination with a xanthine oxidase inhibitor, wherein the xanthine oxidase inhibitor is febuxostat. In some embodiments, crystalline Compound 1 is administered in combination with a xanthine oxidase inhibitor, wherein the xanthine oxidase inhibitor is topiroxostat. In some embodiments, crystalline Compound 1 is administered in combination with a xanthine oxidase inhibitor, wherein the xanthine oxidase inhibitor is ositol.

In some embodiments, crystalline Compound 1 and the xanthine oxidase inhibitor are administered in combination in a single dosage form. In some embodiments, crystalline Compound 1 and the xanthine oxidase inhibitor are administered in combination in separate dosage forms.

In some embodiments, crystalline Compound 1 is administered in combination with an SGLT2 inhibitor. In some embodiments, crystalline Compound 1 is administered in combination with an SGLT2 inhibitor, wherein the SGLT2 inhibitor is canagliflozin, dapagliflozin, empagliflozin, empagliflozin/linagliptin, empagliflozin/metformin, or dapagliflozin/metformin. In some embodiments, crystalline Compound 1 is administered in combination with an SGLT2 inhibitor, wherein the SGLT2 inhibitor is canagliflozin. In some embodiments, crystalline Compound 1 is administered in combination with an SGLT2 inhibitor, wherein the SGLT2 inhibitor is dapagliflozin. In some embodiments, crystalline Compound 1 is administered in combination with an SGLT2 inhibitor, wherein the SGLT2 inhibitor is empagliflozin. In some embodiments, crystalline Compound 1 is administered in combination with an SGLT2 inhibitor, wherein the SGLT2 inhibitor is empagliflozin/linagliptin. In some embodiments, crystalline Compound 1 is administered in combination with an SGLT2 inhibitor, wherein the SGLT2 inhibitor is empagliflozin/metformin. In some embodiments, crystalline Compound 1 is administered in combination with an SGLT2 inhibitor, wherein the SGLT2 inhibitor is dapagliflozin/metformin.

In some embodiments, crystalline Compound 1 and the SGLT2 inhibitor are administered in combination in a single dosage form. In some embodiments, crystalline Compound 1 and the SGLT2 inhibitor are administered in combination in separate dosage forms.

In some embodiments, crystalline Compound 1 is administered in combination with a xanthine oxidase inhibitor and an SGLT2 inhibitor. In some embodiments, crystalline Compound 1 is administered in combination with a xanthine oxidase inhibitor and an SGLT2 inhibitor, wherein the xanthine oxidase inhibitor is allopurinol, oxypurinol, febuxostat, topiroxostat, or inositol, and the SGLT2 inhibitor is canagliflozin, dapagliflozin, empagliflozin, empagliflozin/linagliptin, empagliflozin/metformin, or dapagliflozin/metformin.

In some embodiments, crystalline Compound 1, the xanthine oxidase inhibitor, and the SGLT2 inhibitor are administered in combination in a single dosage form. In some embodiments, crystalline Compound 1, the xanthine oxidase inhibitor, and the SGLT2 inhibitor are administered in combination in separate dosage forms.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the physician after evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is crystalline Compound 1 described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

The dosage regimen to treat, prevent, or ameliorate the condition(s) for which relief is sought, can be modified in accordance with a variety of factors. These factors include the disorder or condition from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from a few minutes to several hours, depending upon the properties of each pharmaceutical agent such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is correlated with certain diseases or conditions.

The compounds described herein and combination therapies can be administered before, during, or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The initial administration can be via any route practical, such as, for example, an intravenous injection, a bolus injection, infusion over about 5 minutes to about 5 hours, a pill, a capsule, transdermal patch, buccal delivery, and the like, or combination thereof. A compound is preferably administered as soon as is practicable after the onset of a disease or condition is detected or suspected, and for a length of time necessary for the treatment of the disease or condition. The length of treatment can vary for each subject, and the length can be determined using specified criteria.

Kits/Articles of Manufacture

For use in the therapeutic methods of use described herein, kits and articles of manufacture are also described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Packaging materials for use in packaging pharmaceutical products include, e.g., U.S. Pat. No. 5,323,907. Examples of pharmaceutical packaging materials include, but are not limited to, blister packs, bottles, tubes, bags, containers, bottles, and any packaging material suitable for a selected formulation and intended mode of administration and treatment.

In some embodiments, the compounds or compositions described herein, are presented in a package or dispenser device which may contain one or more unit dosage forms containing the active ingredient. The compound or composition described herein is packaged alone, or packaged with another compound or another ingredient or additive. In some embodiments, the package contains one or more containers filled with one or more of the ingredients of the pharmaceutical compositions. In some embodiments, the package comprises metal or plastic foil, such as a blister pack. In some embodiments, the package or dispenser device is accompanied by instructions for administration, such as instructions for administering the compounds or compositions for treating a neoplastic disease. In some embodiments, the package or dispenser is accompanied with a notice associated with the container in form prescribed by a governmental agency regulating the manufacture, use, or sale of pharmaceuticals, which notice is reflective of approval by the agency of the form of the drug for human or veterinary administration. In some embodiments, such notice, for example, is the labeling approved by the U.S. Food and Drug Administration for prescription drugs, or the approved product insert. In some embodiments, compositions include a compound described herein formulated in a compatible pharmaceutical carrier are prepared, placed in an appropriate container, and labeled for treatment of an indicated condition.

For example, the container(s) include crystalline Compound 1, optionally in a composition or in combination with another agent as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

EXAMPLES

List of Abbreviations

As used throughout the description of the invention, the following abbreviations, unless otherwise indicated, shall be understood to have the following meanings:

ACN or MeCN acetonitrile
Bn benzyl
BOC or Boc tert-butyl carbamate
t-Bu tert-butyl
Cy cyclohexyl
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
eq or equiv equivalent(s)
Et ethyl
$Et_2O$ diethyl ether
EtOH ethanol
EtOAc ethyl acetate
HPLC high performance liquid chromatography
Me methyl
MeOH methanol
MS mass spectroscopy
GC gas chromatography
h hour(s)
KF Karl Fischer
min minutes
MsOH methanesulfonic acid
NMR nuclear magnetic resonance
RP-HPLC reverse phase-high performance liquid chromatography
r.t. room temperature
TFA trifluoroacetic acid
THF tetrahydrofuran
TLC thin layer chromatography
V volumes

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted.

Example 1: Preparation of (3,5-dibromo-4-hydroxyphenyl)(2-(1-hydroxyethyl)benzofuran-3-yl-4,5,6,7-$d_4$)methanone (Compound 1)

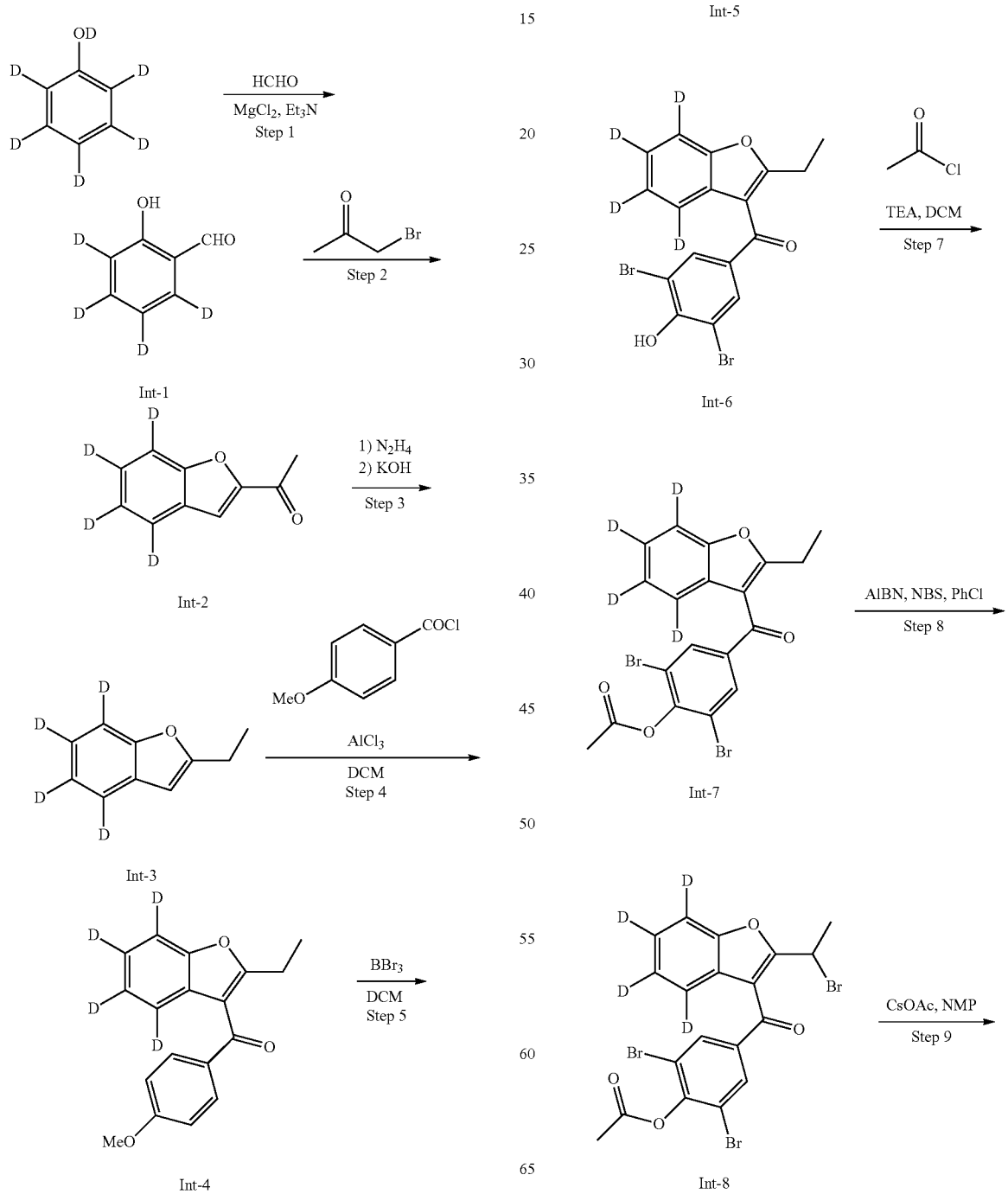

-continued

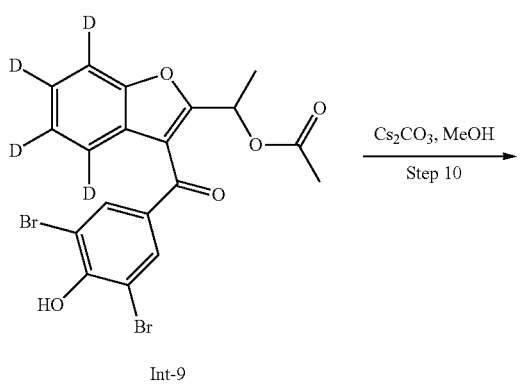

Int-9

↓ Cs₂CO₃, MeOH
Step 10

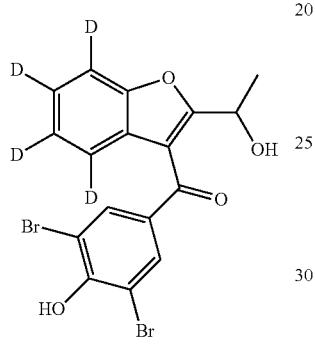

Compound 1

Step 1: 2-Hydroxybenzaldehyde-3,4,5,6-d₄ (Int-1)

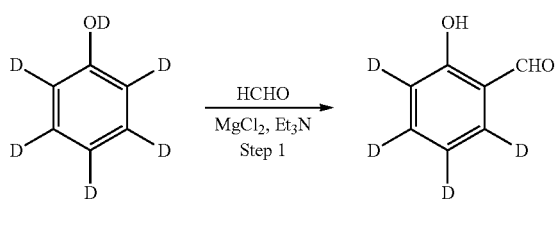

Int-1

A solution of phen-d₆-ol (1.0 eq), magnesium chloride (1.5 eq), and triethylamine (3.7 eq) in ACN (10 V) was stirred at 20° C. for 0.5 h. Formaldehyde (8.0 eq) was added and the reaction mixture was heated at reflux for 3 h. The reaction mixture was cooled to room temperature and 10% HCl solution (10V) was added. The mixture was extracted with EtOAc (3×6V). The combined organic layers were washed with brine (6 V), dried with Na₂SO₄, and concentrated to give 2-hydroxybenzaldehyde-3,4,5,6-d₄ (Int-1) as a yellow oil.

Step 2: 1-(Benzofuran-2-yl-4,5,6,7-d₄)ethan-1-one (Int-2)

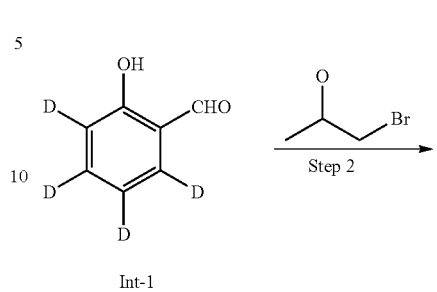

Int-1

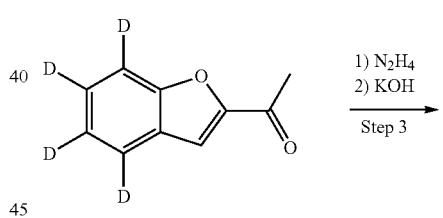 

Int-2

A solution of 2-hydroxybenzaldehyde-3,4,5,6-d₄ (Int-1) (1.0 eq), bromopropanone (1.0 eq), and potassium carbonate (3.0 eq) in acetone (14 V) was heated at reflux for 6 h. The reaction mixture was cooled to room temperature and filtered. The filtrate was concentrated and the crude product recrystallized (petroleum ether/EtOAc 10:1) to give 1-(benzofuran-2-yl-4,5,6,7-d₄)ethan-1-one (Int-2) as a yellow solid.

Step 3: 2-Ethylbenzofuran-4,5,6,7-d₄ (Int-3)

Int-2

1) N₂H₄
2) KOH
Step 3

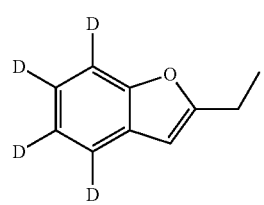

Int-3

A solution of 1-(benzofuran-2-yl-4,5,6,7-d₄)ethan-1-one (Int-2) (1.0 eq) in diethylene glycol (16 V) was heated at 120° C. N2H4·H₂O (2.0 eq) and water (1V) was added. The reaction mixture was heated at 180° C. for 10 min and then cooled to 120° C. KOH (2.0 eq) was added and the reaction mixture was heated at 120° C. for 6 h. The reaction mixture was cooled, poured into water, and extracted with EtOAc (20 V×3). The combined organic layers were washed with brine (20 V) and concentrated to give 2-ethylbenzofuran-4,5,6,7-d₄ (Int-3) as a colorless oil.

Step 4: (2-Ethylbenzofuran-3-yl-4,5,6,7-d₄)(4-methoxyphenyl)methanone (Int-4)

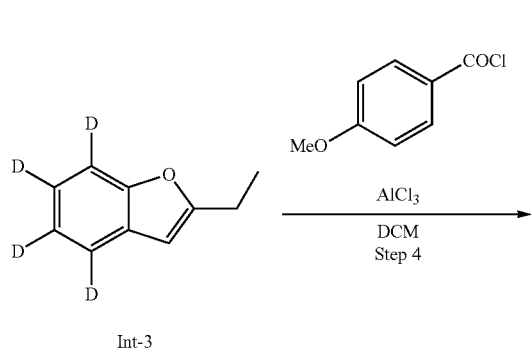

Int-3

A solution of 2-ethylbenzofuran-4,5,6,7-d₄ (Int-3) (1.0 eq) and 4-methoxybenzoyl chloride (1.15 eq) in DCM (30 V) was cooled to 0° C. and charged with AlCl₃ (1.1 eq). The reaction mixture was stirred for 2 h at 0° C. D₂O (2 V) was added to the mixture dropwise at 5° C. and the mixture was stirred for 0.5 h. Water (8 V) was added. The organic layer was separated, washed with brine (10 V), dried with Na₂SO₄, and concentrated under vacuum at 40° C. to give (2-ethylbenzofuran-3-yl-4,5,6,7-d₄)(4-methoxyphenyl)methanone (Int-4) as a yellow solid. ¹H NMR (400 MHz, DMSO-d₆): δ 7.81-7.77 (dd, 2H), 7.12-7.08 (dd, 2H), 3.88 (s, 3H), 2.86-2.78 (q, 2H), 1.28-1.23 (t, 3H); LCMS: 285 [M+H]⁺.

Step 5: (2-Ethylbenzofuran-3-yl-4,5,6,7-d₄)(4-hydroxyphenyl)methanone (Int-5)

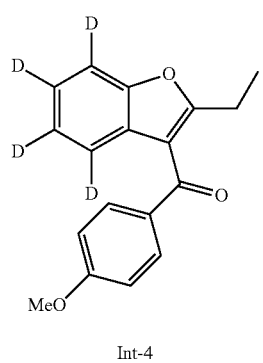

Int-4

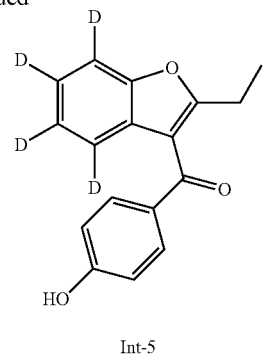

Int-5

To a solution of (2-ethylbenzofuran-3-yl-4,5,6,7-d₄)(4-methoxyphenyl)methanone (Int-4) (1.0 eq) in DCM (10 V) at 0° C. was added BBr₃ (2.2 eq) dropwise at 0-5° C. The reaction mixture was warmed to room temperature and stirred for 14 h. Ice water (10 V) was added and the mixture was stirred for 0.5 h. The organic layer was separated, washed with brine (10 V), dried with Na₂SO₄, and concentrated under vacuum at 40° C. to give (2-ethylbenzofuran-3-yl-4,5,6,7-d₄)(4-hydroxyphenyl)methanone (Int-5) as a brown solid. ¹H NMR (400 MHz, DMSO-d₆): δ 10.47 (s, 1H), 7.71-7.68 (dd, 2H), 6.92-6.88 (dd, 2H), 2.84-2.78 (q, 2H), 1.28-1.24 (t, 3H); LCMS: 271 [M+H]⁺.

Step 6: (3,5-Dibromo-4-hydroxyphenyl)(2-ethylbenzofuran-3-yl-4,5,6,7-d₄)methanone (Int-6)

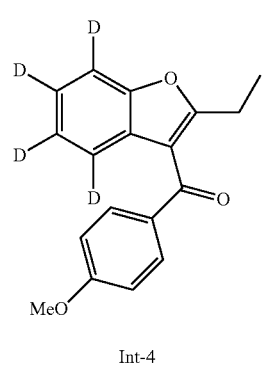

Int-5

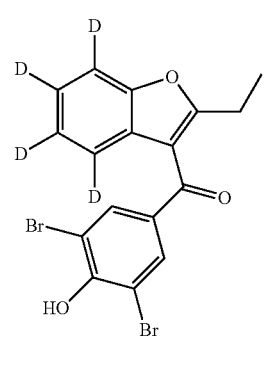

Int-6

To a solution of (2-ethylbenzofuran-3-yl-4,5,6,7-d₄)(4-hydroxyphenyl)methanone (Int-5) (1.0 eq) in DCM (10 V) at 10° C. was added NBS (1.7 eq) dropwise at 0-5° C. The reaction mixture was warmed to 18° C. and stirred for 16 h.

The reaction mixture was charged with additional NBS (0.14 eq) at 10° C. and stirred for 16 h at 18° C. The reaction mixture was charged with additional NBS (0.05 eq) at 10° C. and stirred for 3 h at 18° C. Water (15 V) was added and the mixture was stirred for 0.5 h. The organic layer was separated, washed with brine (15 V), dried with $Na_2SO_4$, and concentrated under vacuum at 40° C. to give a yellow solid. The yellow solid was slurried in EtOAc/n-heptane (1 V/10 V) at 60° C. for 2 h. The mixture was cooled to 10° C. and filtered to give (3,5-dibromo-4-hydroxyphenyl)(2-ethylbenzofuran-3-yl-4,5,6,7-$d_4$)methanone (Int-6) as a yellow solid. $^1$H NMR (400 MHz, DMSO-$d_6$): δ 11.05 (s, 1H), 7.92 (s, 2H), 2.84-2.75 (q, 2H), 1.27-1.20 (t, 3H); LCMS: 429 [M+H]$^+$.

Step 7: 2,6-Dibromo-4-(2-ethylbenzofuran-3-carbonyl-4,5,6,7-$d_4$)phenyl acetate (Int-7)

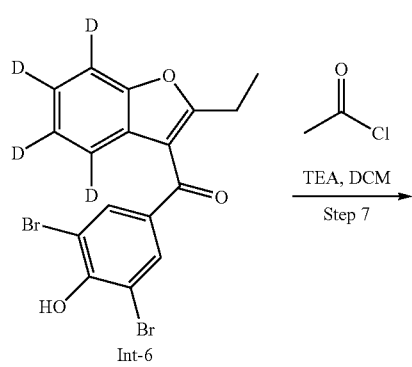

Int-6

To a solution of (3,5-dibromo-4-hydroxyphenyl)(2-ethylbenzofuran-3-yl-4,5,6,7-$d_4$)methanone (Int-6) (1.0 eq) and triethylamine (2.5 eq) in DCM (10 V) at 0° C. was added acetyl chloride (2.0 eq) dropwise at 0-5° C. The reaction mixture was warmed to 15° C. and stirred for 2 h. Water (10 V) was added. The organic layer was separated, washed with brine (10 V), dried with $Na_2SO_4$, and concentrated under vacuum at 40° C. to give a crude solid. The crude solid was decolorized with activated charcoal (0.5 w/w) in EtOAc (10 V) at 50° C. for 1 h. The mixture was cooled to 30° C. and filtered with kieselguhr aid to remove the activated charcoal. The filtrate was concentrated under vacuum at 40° C. The residue was dissolved in i-PrOH (2 V) and heated at 60° C. for 1 h. The solution was cooled to 45° C., charged with seed crystals (0.5% w/w), and stirred for 1 h. The mixture was cooled to 25° C. and stirred for 16 h. The mixture was filtered and the solid dried to give 2,6-dibromo-4-(2-ethylbenzofuran-3-carbonyl-4,5,6,7-$d_4$)phenyl acetate (Int-7) as a yellow solid. $^1$H NMR (400 MHz, DMSO-$d_6$): δ 8.08 (s, 2H), 2.81-2.74 (q, 2H), 2.44 (s, 3H), 1.27-1.22 (t, 3H); LCMS: 471 [M+H]$^+$.

Step 8: 2,6-dibromo-4-(2-(1-bromoethyl)benzofuran-3-carbonyl-4,5,6,7-$d_4$)phenyl acetate (Int-8)

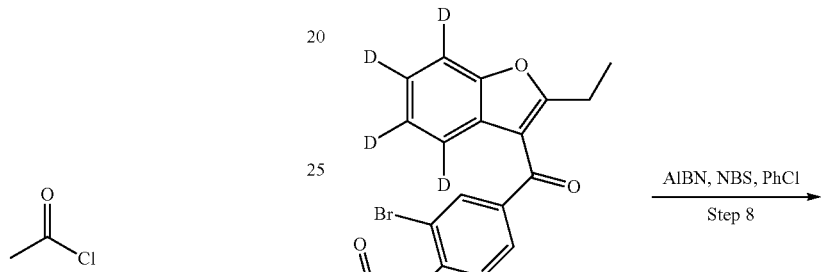

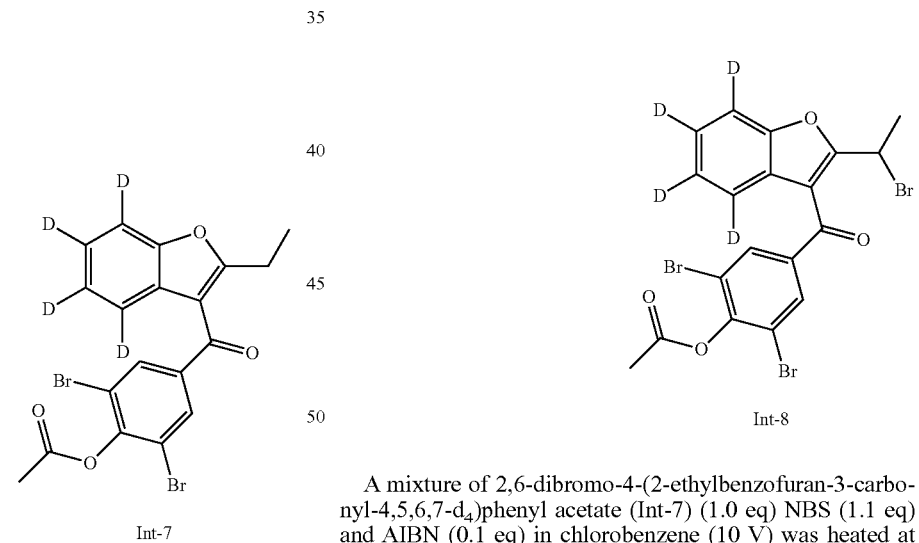

A mixture of 2,6-dibromo-4-(2-ethylbenzofuran-3-carbonyl-4,5,6,7-$d_4$)phenyl acetate (Int-7) (1.0 eq) NBS (1.1 eq) and AIBN (0.1 eq) in chlorobenzene (10 V) was heated at 55° C. for 6 h with stirring. The reaction mixture was cooled to 25° C., water (10 V) was added, and the mixture stirred for 1 h. The organic layer was separated, dried with $Na_2SO_4$, and concentrated to 1.5 to 2 V under vacuum. The solution was charged with heptane (5 V) and concentrated to 1.5 to 2 V under vacuum. This was repeated three times. The solution was charged with heptane (3 V), cooled to 5° C., and stirred for 4 h. The mixture was filtered and the solid washed with heptane (1 V×2), and dried to give 2,6-dibromo-4-(2-(1-bromoethyl)benzofuran-3-carbonyl-4,5,6,7-$d_4$)phenyl acetate (Int-8) as a yellow solid. $^1$H NMR (400 MHz, DMSO-$d_6$): δ 8.11 (s, 2H), 5.47-5,40 (q, 1H), 2.46 (s, 3H), 2.05-2.03 (d, 3H); LCMS: 469 [M+H−HBr]$^+$.

Step 9: 1-(3-(3,5-Dibromo-4-hydroxybenzoyl)benzofuran-2-yl-4,5,6,7-$d_4$)ethyl acetate (Int-9)

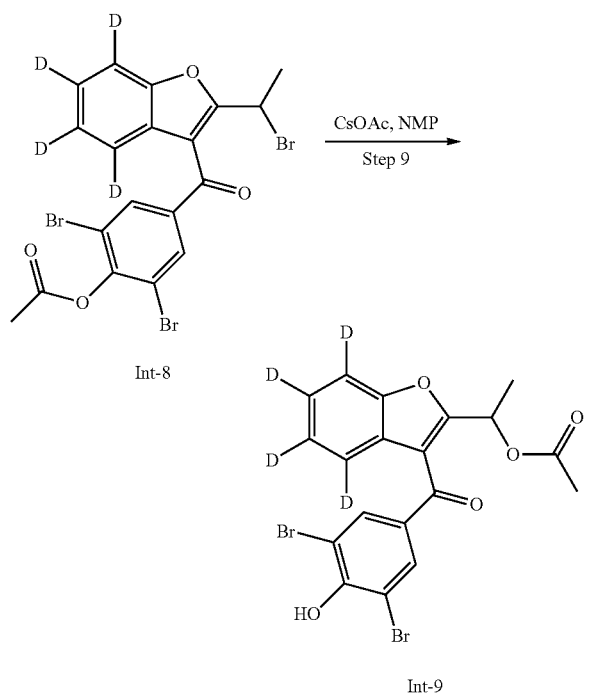

A mixture of 2,6-dibromo-4-(2-(1-bromoethyl)benzofuran-3-carbonyl-4,5,6,7-$d_4$)phenyl acetate (Int-8) (1.0 eq) and CsOAc (5.0 eq) in N-methylpyrrolidine (8 V) was stirred at 25° C. for 12 h. The reaction mixture was filtered. To the filtrate was added water (15 V) and EtOAc (10 V). The pH of the resulting mixture was adjusted to 2-3 with 12 N HCl. The mixture was stirred for 1 h and then let stand for 0.5 h. The organic solution was collected and the aqueous solution extracted with EtOAc (10 V). The combined organic solution was washed with water (10 V×3), dried with $Na_2SO_4$, and concentrated under vacuum. The residue was purified by silica gel chromatography to give 1-(3-(3,5-dibromo-4-hydroxybenzoyl)benzofuran-2-yl-4,5,6,7-$d_4$) ethyl acetate (Int-9) as an off-white solid. $^1$H NMR (400 MHz, DMSO-$d_6$): δ 7.93 (s, 2H), 5.88-5.87(q, 1H), 1.99 (s, 3H), 1.63-1.61 (d, 3H); LCMS: 427 [M+H—$CH_3CO_2H$]$^+$.

Step 10: (3,5-Dibromo-4-hydroxyphenyl)(2-(1-hydroxyethyl)benzofuran-3-yl-4,5,6,7-$d_4$)methanone (Compound 1)

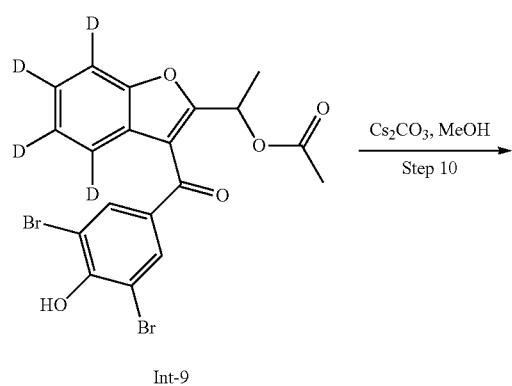

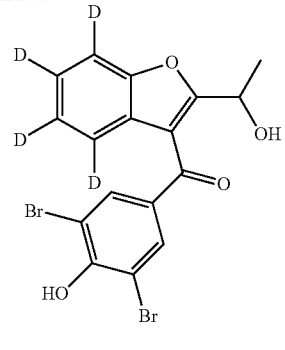

Compound 1

To a mixture of 1-(3-(3,5-dibromo-4-hydroxybenzoyl)benzofuran-2-yl-4,5,6,7-$d_4$)ethyl acetate (Int-9) (1.0 eq) in methanol (10 V) was added $Cs_2CO_3$ (3.0 eq). The reaction mixture was stirred at 28° C. for 12 h. Water (20 V) was added and the pH of the resulting mixture was adjusted to 2-3 with 12 N HCl. The mixture was stirred for 1 h. The mixture was filtered and the filter cake was washed with water (2 V×2). A solution of the filter cake, EtOAc (15 V) and 1 N HCl (5 V) was stirred for 1 h at 25° C. The organic solution was collected, dried with $Na_2SO_4$, and concentrated to 2 to 3 V under vacuum. The solution was heated at 50° C. for 1 h, charged with seed crystals (1% w/w), and heated at 50° C. for 2 h. n-Heptane (10 V) was added dropwise and the mixture was heated at 50° C. for 2 h. the mixture was cooled to 25° C. and stirred for 12 hours. The solid was collected by filtration and dried to give (3,5-dibromo-4-hydroxyphenyl)(2-(1-hydroxyethyl)benzofuran-3-yl-4,5,6,7-$d_4$)methanone (Compound 1) as an off-white solid. $^1$H NMR (400 MHz, DMSO-$d_6$): δ 11.11 (bs, 1H), 7.95 (s, 1H), 5.60 (bs, 1H), 4.88-4.83 (q, 1H), 1.49-1.48 (d, 3H); LCMS: 427 [M+H—$H_2O$]$^+$.

II. Characterization of Polymorphs

Example 2: X-Ray Powder Diffraction (XRPD)

X-ray powder diffraction studies were performed using a Bruker D8 Advance with the following instrument parameters:

Scan: 3° (2θ) to 40° (2θ)
Increment: 0.02° (2θ)
Scan speed: 0.3 sec/step
Voltage: 40 KV
Current: 40 mA
Rotation: On
Sample hold: Zero-background sample holder XRPD analysis of Form 3 of Compound 1 (FIG. 1) showed Form 3 to be crystalline with characteristic peaks at 6.8° 2-Theta, 13.6° 2-Theta, 14.6° 2-Theta, 21.2° 2-Theta, 24.2° 2-Theta, 24.7° 2-Theta, 26.7° 2-Theta, and 27.5° 2-Theta.

XRPD analysis of Form 2 of Compound 1 (FIG. 4) showed Form 2 to be crystalline with characteristic peaks at 8.3° 2-Theta, 10.7° 2-Theta, 16.6° 2-Theta, 19.7° 2-Theta, 23.7° 2-Theta, 25.0° 2-Theta, 25.6° 2-Theta, and 27.1° 2-Theta.

XRPD analysis of Form 1 of Compound 1 (FIG. 7) showed Form 1 to be crystalline with characteristic peaks at 5.6° 2-Theta, 11.5° 2-Theta, 13.8° 2-Theta, 14.3° 2-Theta, 17.0° 2-Theta, 18.9° 2-Theta, 27.9° 2-Theta, and 31.4° 2-Theta.

Example 3: Polarized Light Microscopy (PLM)

Light microscopy studies were performed using a Nikon Eclipse LV100N POL. The solid was placed on the glass slide and dispersed by cedar oil, then observed with suitable magnification.

PLM analysis of Form 3 of Compound 1 showed irregular crystals, sizes up to 50 μm.

PLM analysis of Form 2 of Compound 1 showed irregular particles, sizes up to 100 μm.

PLM analysis of Form 1 of Compound 1 showed needle-like crystals, sizes up to 50 μm.

Example 4: Thermogravimetric Analysis

Thermogravimetric analysis of solid was performed using TA Discovery TGA 55 or equivalent. The sample was placed in an open aluminum pan, the amount was weighed automatically. The sample was heated at the heating rate of 10° C./min up to the final temperature.

TGA of Form 3 of Compound 1 (FIG. 2) showed no weight loss before decomposition with onset at about 147° C.

TGA of Form 2 of Compound 1 (FIG. 5) showed no weight loss before decomposition with onset at about 139° C.

TGA of Form 1 of Compound 1 (FIG. 8) showed about 4% weight loss prior to 100° C. consistent with a monohydrate.

Example 5: Differential Scanning Calorimetry (DSC)

DSC studies were performed using a TA Discovery DSC 250. The sample was weighed in pinhole aluminum pan and the accurate amount was recorded. The sample was heated at the heating rate of 10° C./min with 50 mL/min nitrogen purge from 25° C. up to the final temperature.

DSC analysis of Form 3 of Compound 1 (FIG. 3) showed a sharp melting endotherm with onset at 147° C. (81 J/g).

DSC analysis of Form 2 of Compound 1 (FIG. 6) showed a sharp melting endotherm with onset at 139° C. (77 J/g).

DSC analysis of Form 1 of Compound 1 (FIG. 9) showed a broad endotherm with onset at 80° C. (74 J/g).

Example 6: Dynamic Vapor Sorption (DVS)

Figure 10:
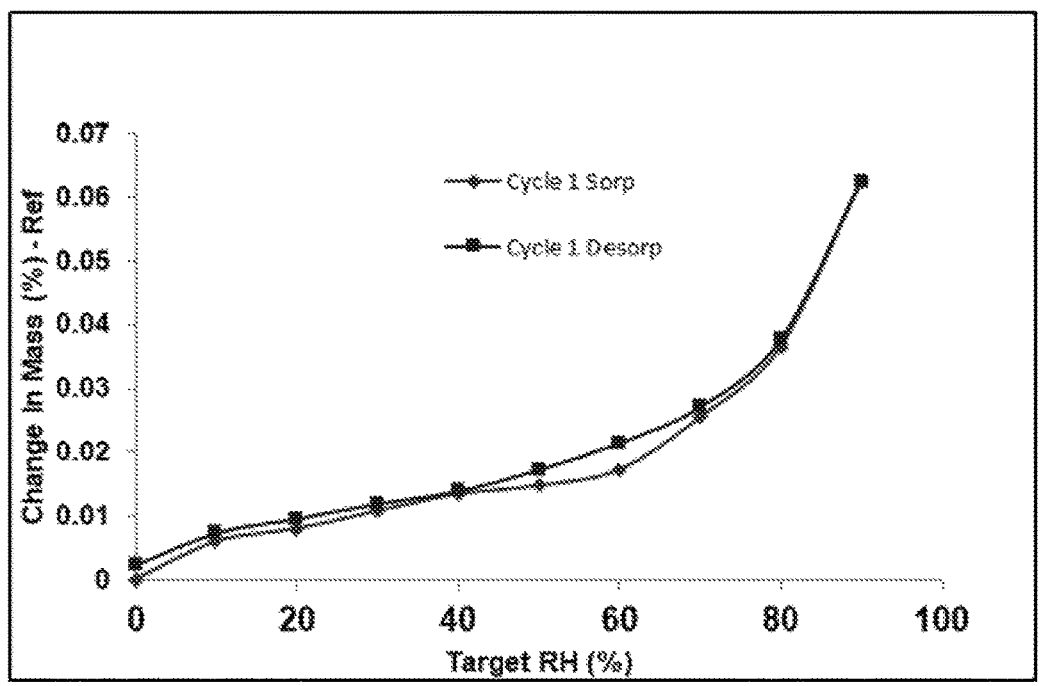
FIG. 10. Illustrates a gravimetric vapor sorption (GVS) analysis of crystalline (3,5-dibromo-4-hydroxyphenyl)(2-(1-hydroxyethyl)benzofuran-3-yl-4,5,6,7-$d_4$)methanone (Compound 1), Form 3.

DVS studies were performed using a DVS Intrinsic (SMS, UK) or IGASORP (Hiden, UK). 10 to 50 mg of compound was transferred into the DVS and the weight change recorded with respect to a varying atmospheric humidity at 25° C. using the following parameters:
Drying at 40° C. until dm/dt<±0.002%/min
Min time: 30 min, Max time: 120 min (for IGASORP)
Equilibrium: 60 min
Cycle: 0, 5, 10, 20, 30, 40, 50, 60, 70, 80, 90, 80, 70, 60, 50, 40, 30, 20, 10, 5, 0
Characterize the sample after the DVS experiment by XRPD The DVS analysis of Form 3 of Compound 1 (FIG. 10) showed 0.04% moisture uptake between 0-90% RH. Post-GVS analysis by XRPD showed no change. The material was non-hygroscopic.

Figure 11:
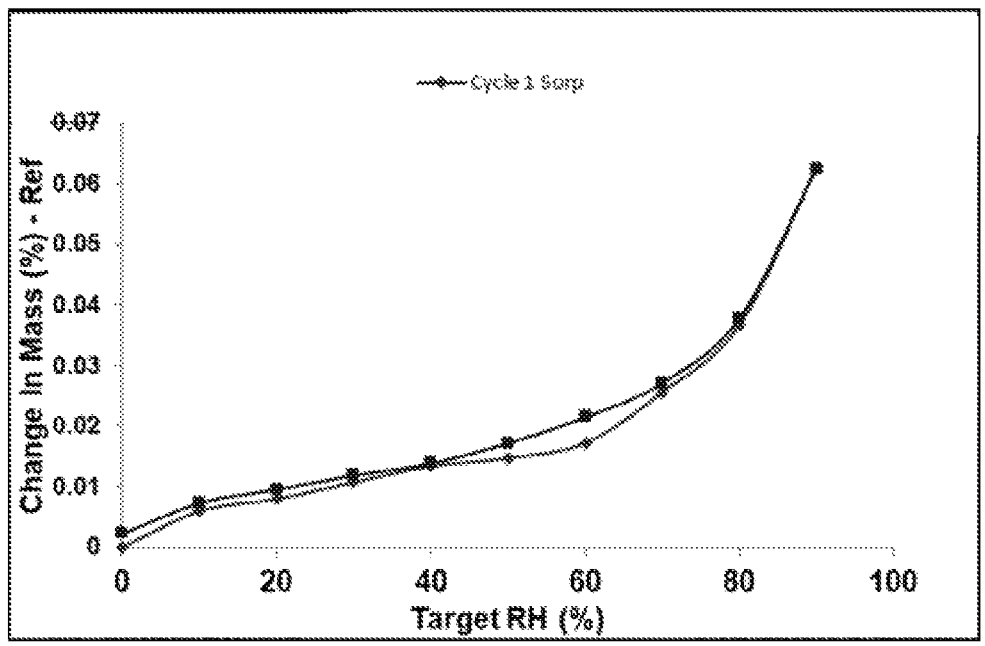
FIG. 11. Illustrates a gravimetric vapor sorption (GVS) analysis of crystalline (3,5-dibromo-4-hydroxyphenyl)(2-(1-hydroxyethyl)benzofuran-3-yl-4,5,6,7-$d_4$)methanone (Compound 1), Form 2.

The DVS analysis of Form 2 of Compound 1 (FIG. 11) showed 0.08% moisture uptake between 0-90% RH. Post-GVS analysis by XRPD showed no change. The material was non-hygroscopic.

Figure 12:
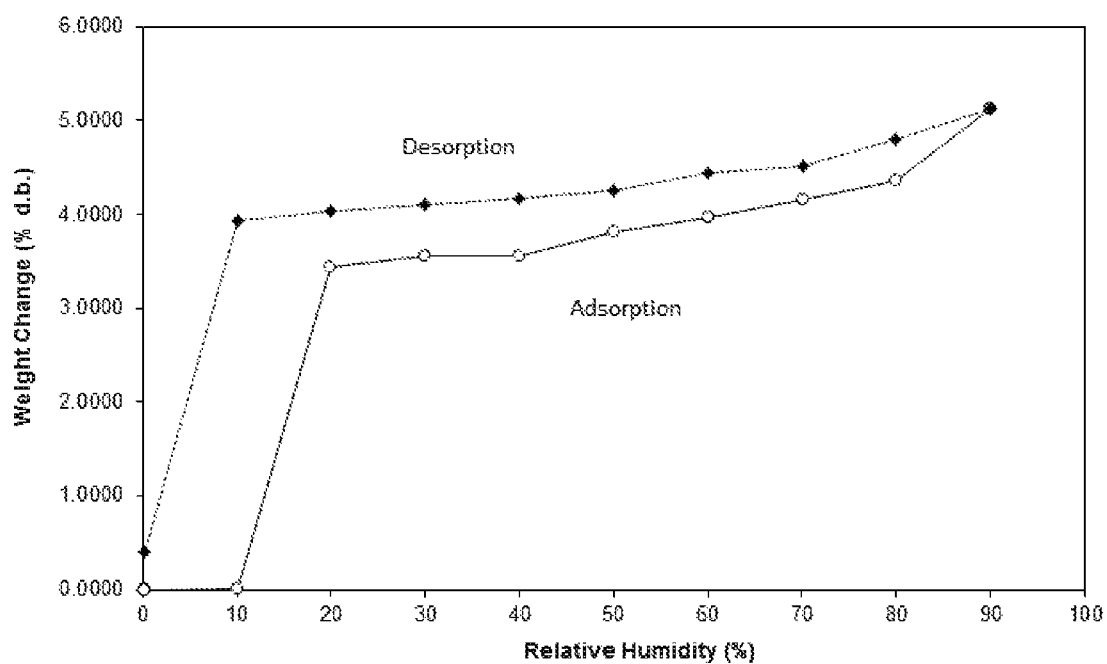
FIG. 12. Illustrates a gravimetric vapor sorption (GVS) analysis of crystalline (3,5-dibromo-4-hydroxyphenyl)(2-(1-hydroxyethyl)benzofuran-3-yl-4,5,6,7-$d_4$)methanone (Compound 1), Form 1.

The DVS analysis of Form 1 of Compound 1 (FIG. 12) showed the dehydrated form converted to hydrated form at RH ≥20%.

III. Polymorph Screen

Compound 1, Form 1, was used for the polymorph screen Examples 7, 8, and 9.

Example 7: Binary Solvent Study

The binary solvent study was performed using a combination of 13 solvents (acetone, acetonitrile, 2-butanone, ethanol, ethyl acetate, heptane, isopropanol, isopropyl acetate, methanol, methyl t-butyl ether (MTBE), tetrahydrofuran (THF), toluene, and water) utilizing slow evaporation. 91 vials each containing Compound 1, Form 1 (40-80 mg) were filled with 3 mL of solvent. 2 mL of the Compound 1 solution/suspension was filtered into a centrifuge tube (the remaining 1 mL of Compound 1 suspensions were used in Example 8). 100 μL of each filtrate was distributed in 96-well plates. The plate was covered by sealing film with pin holes and allowed to slowly evaporate in a fume hood under ambient conditions. 21 solid samples were tested by XRPD. Results are shown in Table 1.

TABLE 1

| Sample | Solvent 1 | Solvent 2 | XRPD result |
|---|---|---|---|
| S-1 | Methanol | Methanol | Form 1 |
| S-2 | Methanol | Methanol | Form 1 |
| S-3 | Methanol | Ethanol | Form 1 |
| S-4 | Methanol | Isopropanol | Form 1 |
| S-5 | Methanol | Heptane | Form 1 |
| S-6 | Methanol | Acetone | Form 1 |
| S-7 | Methanol | water | Form 1 |
| S-8 | Methanol | Ethyl acetate | Form 1 |
| S-9 | Methanol | Isopropyl acetate | Form 1 |
| S-10 | Ethanol | Isopropanol | Form 1 |
| S-11 | Isopropanol | Isopropanol | Form 1 |
| S-12 | Isopropanol | Heptane | Form 1 |
| S-13 | Heptane | THF | Form 1 |
| S-14 | 2-butanone | Acetone | Form 1 |
| S-15 | 2-butanone | Ethyl acetate | Form 1 |
| S-16 | Acetonitrile | Acetonitrile | Form 1 |
| S-17 | Acetonitrile | MTBE | Form 1 |
| S-18 | MTBE | MTBE | Form 1 |
| S-19 | MTBE | Toluene | Form 1 |
| S-20 | Ethyl acetate | Ethyl acetate | Form 1 |
| S-21 | Ethyl acetate | Isopropyl acetate | Form 1 |

Example 8: Slurry Study

The remaining Compound 1 suspensions from Example 7 were stirred for four days. The solid was collected by filtration and analyzed by XRPD. In addition, slurries of Compound 1, Form 1 (50 mg) in 1.5 mL of solvent were heated at 50° C. for a specified time. The solid was collected by filtration and analyzed by XRPD. Results are shown in Table 2.

TABLE 2

| Solvent | Temperature | Time | XRPD |
|---|---|---|---|
| Heptane | r.t. | 4 d | Form 1 |
| Toluene | r.t. | 4 d | Form 1 |
| H₂O | r.t. | 4 d | Form 1 |
| Heptane | 50° C. | 7 h | Form 2 |
| H₂O | 50° C. | 7 h | Form 1 |

Example 9: Anti-Solvent Precipitation Study

Compound 1, Form 1 (ca. 50 mg) was weighed into sample vials and various solvents were added to dissolve the solid. Heptane was gradually added to make a suspension and the suspension was stirred at room temperature or 50° C. for a specified time. Any solids were collected by filtration and analyzed by XRPD. Results are shown in Table 3.

TABLE 3

| Solvent | Solvent volume (μL) | Anti-solvent volume (μL) | Temp | Time | Result |
|---|---|---|---|---|---|
| Methyl acetate | 200 | 100 | r.t. | 1 h | Form 1 |
| Ethyl acetate | 300 | 100 | r.t. | 1 h | Form 1 |
| IPA | 300 | 100 | r.t. | 1 h | Form 1 |
| 2-butanone | 500 | 100 | r.t. | 1 h | Form 1 |
| Isopropyl acetate | 400 | 1300 | r.t. | 1 h | Form 1 |
| Methyl acetate | 200 | 3000 | 50° C. | Overnight | Form 1 |
| Ethyl acetate | 300 | 3000 | 50° C. | Overnight | Form 2 |
| IPA | 300 | 3000 | 50° C. | Overnight | Form 1 |
| 2-butanone | 500 | 3000 | 50° C. | Overnight | Form 1 |
| Isopropyl acetate | 400 | 3000 | 50° C. | Overnight | Form 1 |
| Toluene | 3000 | 5000 | 50° C. | 6 h | Form 3 |

Example 10: Interconversion Study

The same amount of Compound 1, Form 2 and Compound 1, Form 3 were added to EtOAc/heptane mixtures and stirred at room temperature (r.t.) or 50° C. for a specified time. The solid was collected by filtration and analyzed by XRPD. Interconversion results showed that Form 3 was the more stable form at high temperature and r.t. Results are shown in Table 4.

TABLE 4

| Form 2 (mg) | Form 3 (mg) | Anti-solvent volume (μL) | Temp | Time | Result |
|---|---|---|---|---|---|
| 12 | 12 | EtOAc - heptane (1:9), 30 V | 50 | Overnight | Form 3 |
| 21 | 21 | EtOAc - heptane (2:8), 20 V | r.t | 2 d | Form 3 |

IV. Biological Data

Example 11: In Vitro Interaction Studies of Compound 1 and Benzbromarone with the Human URAT1 Uptake Transporter Uptake experiments were performed using MDCKII cells stably expressing the human URAT1 uptake transporter. Cells were cultured at 37±1° C. in an atmosphere of 95:5 air:$CO_2$ and were plated onto standard 96-well tissue culture plates at the cell number described in Table 5.

TABLE 5

| Transporter | Control cell line | Cell number/ well | Culturing medium | Incubation prior to the assay | Buffer |
|---|---|---|---|---|---|
| human URAT1 | Mock-transfected MDCKII | $1 \times 10^5$ | DMEM 4.5 g/L glucose | 24 h | HBSS w/o $Cl^-$ (pH 7.4) |

DMEM: Dulbecco's Modified Eagle's Medium;
HBSS: Hank's balanced salt solution; w/o: without Before the experiment, the medium was removed and the cells were washed twice with 100 μL of HBSS without $Cl^-$. Uptake experiments were carried out at 37±1° C. in 50 μL of HBSS without $Cl^-$, pH 7.4 containing the probe substrate (20 μM uric acid) and the test article (TA) or solvent. The organic solvent concentration was equal in all wells, and did not exceed 1% (v/v).

Treatment groups are presented in Table 6.

TABLE 6

| Treatment groups in the 96-well plate format | No. of wells |
|---|---|
| TA in assay buffer (0.01, 0.04, 0.12, 0.37, 1.11, 3.33 and 10.0 μM) in transfected cells | 3 per TA concentration |
| TA in assay buffer (0.01, 0.04, 0.12, 0.37, 1.11, 3.33 and 10.0 μM) in control cells | 3 per TA concentration |
| 1% DMSO control in transfected cells | 3 |
| 1% DMSO control in control cells | 3 |
| Reference inhibitor in assay buffer with 1% DMSO in transfected cells | 3 |
| Reference inhibitor in assay buffer with 1% DMSO in control cells | 3 |

After the experiment, cells were washed twice with 100 μL of ice cold HBSS without $Cl^-$ and lysed with 50 μL of 0.1 M NaOH. Radiolabeled probe substrate transport was determined by measuring an aliquot (35 μL) from each well for liquid scintillation counting.

Results: Both test articles (Compound 1 and benzbromarone) were soluble in HBSS buffer at all tested concentrations; the highest tested concentration being 10 μM. Compound 1 inhibited URAT1 mediated uric acid accumulation by 100% at a concentration of 10 μM with an $IC_{50}=0.067$ μM. Benzbromarone inhibited URAT1 mediated uric acid accumulation by 98% at a concentration of 10 μM with an $IC_{50}=0.196$ μM.

We claim:

1. A crystalline form of (3,5-dibromo-4-hydroxyphenyl)(2-(1-hydroxyethyl)benzofuran-3-yl-4,5,6,7-$d_4$)methanone, wherein the crystalline form of (3,5-dibromo-4-hydroxyphenyl)(2-(1-hydroxyethyl)benzofuran-3-yl-4,5,6,7-$d_4$)methanone is Form 3 having at least one of the following properties:
    (a) an X-ray powder diffraction (XRPD) pattern with characteristic peaks at 6.8° 2-Theta, 13.6° 2-Theta, 14.6° 2-Theta, 21.2° 2-Theta, 24.2° 2-Theta, 24.7° 2-Theta, 26.7° 2-Theta, and 27.5° 2-Theta;
    (b) a DSC thermogram with an endotherm having an onset at 147° C.; or
    (c) a combination thereof.

2. The crystalline form of claim 1, wherein the crystalline form has an X-ray powder diffraction (XRPD) pattern with characteristic peaks at 6.8° 2-Theta, 13.6° 2-Theta, 14.6° 2-Theta, 21.2° 2-Theta, 24.2° 2-Theta, 24.7° 2-Theta, 26.7° 2-Theta, and 27.5° 2-Theta.

3. The crystalline form of claim 1, wherein the crystalline form has a DSC thermogram with an endotherm having an onset at 147° C.

4. The crystalline form of claim 1, wherein the crystalline form is characterized as having properties (a) and (b).

5. A pharmaceutical composition comprising the crystalline form of claim 1, and at least one inactive ingredient selected from pharmaceutically acceptable carriers, diluents, and excipients.

6. A method for treating hyperuricemia or gout in an individual in need thereof, comprising administering to the individual a therapeutically effective amount of a crystalline form of claim 1.

7. A crystalline form of (3,5-dibromo-4-hydroxyphenyl) (2-(1-hydroxyethyl)benzofuran-3-yl-4,5,6,7-$d_4$)methanone, wherein the crystalline form of (3,5-dibromo-4-hydroxyphenyl)(2-(1-hydroxyethyl)benzofuran-3-yl-4,5,6,7-$d_4$)methanone is Form 2 having at least one of the following properties:
  (a) an X-ray powder diffraction (XRPD) pattern with characteristic peaks at 8.3° 2-Theta, 10.7° 2-Theta, 16.6° 2-Theta, 19.7° 2-Theta, 23.7° 2-Theta, 25.0° 2-Theta, 25.6° 2-Theta, and 27.1° 2-Theta;
  (b) a DSC thermogram with an endotherm having an onset at 139° C.; or
  (c) a combination thereof.

8. The crystalline form of claim 7, wherein the crystalline form has an X-ray powder diffraction (XRPD) pattern with characteristic peaks at 8.3° 2-Theta, 10.7° 2-Theta, 16.6° 2-Theta, 19.7° 2-Theta, 23.7° 2-Theta, 25.0° 2-Theta, 25.6° 2-Theta, and 27.1° 2-Theta.

9. The crystalline form of claim 7, wherein the crystalline form has a DSC thermogram with an endotherm having an onset at 139° C.

10. The crystalline form of claim 7, wherein the crystalline form is characterized as having properties (a) and (b).

11. A pharmaceutical composition comprising the crystalline form of claim 7, and at least one inactive ingredient selected from pharmaceutically acceptable carriers, diluents, and excipients.

12. A method for treating hyperuricemia or gout in an individual in need thereof, comprising administering to the individual a therapeutically effective amount of a crystalline form of claim 7.

13. A crystalline form of (3,5-dibromo-4-hydroxyphenyl) (2-(1-hydroxyethyl)benzofuran-3-yl-4,5,6,7-$d_4$)methanone, wherein the crystalline form of (3,5-dibromo-4-hydroxyphenyl)(2-(1-hydroxyethyl)benzofuran-3-yl-4,5,6,7-$d_4$)methanone is Form 1 having at least one of the following properties:
  (a) an X-ray powder diffraction (XRPD) pattern with characteristic peaks at 5.6° 2-Theta, 11.5° 2-Theta, 13.8° 2-Theta, 14.3° 2-Theta, 17.0° 2-Theta, 18.9° 2-Theta, 27.9° 2-Theta, and 31.4° 2-Theta;
  (b) a DSC thermogram with an endotherm having an onset at about 80° C.; or
  (c) a combination thereof.

14. The crystalline form of claim 13, wherein the crystalline form has an X-ray powder diffraction (XRPD) pattern with characteristic peaks at 5.6° 2-Theta, 11.5° 2-Theta, 13.8° 2-Theta, 14.3° 2-Theta, 17.0° 2-Theta, 18.9° 2-Theta, 27.9° 2-Theta, and 31.4° 2-Theta.

15. The crystalline form of claim 13, wherein the crystalline form has a DSC thermogram with an endotherm having an onset at 80° C.

16. The crystalline form of claim 13, wherein the crystalline form is characterized as having properties (a) and (b).

17. A pharmaceutical composition comprising the crystalline form of claim 13, and at least one inactive ingredient selected from pharmaceutically acceptable carriers, diluents, and excipients.

18. A method for treating hyperuricemia or gout in an individual in need thereof, comprising administering to the individual a therapeutically effective amount of a crystalline form of claim 13.

\* \* \* \* \*